United States Patent [19]
Beck et al.

[11] Patent Number: 5,322,680
[45] Date of Patent: Jun. 21, 1994

[54] SUBSTITUTED 2-THIAZOLYL TETRAZOLIUM SALT INDICATORS

[75] Inventors: Gunther Beck, Leverkusen; Jürgen Köcher, Cologne; Klaus Wehling, Wuppertal, all of Fed. Rep. of Germany

[73] Assignee: Miles Inc., Elkhart, Ind.

[21] Appl. No.: 854,773

[22] Filed: Apr. 2, 1992

Related U.S. Application Data

[63] Continuation of Ser. No. 585,650, Sep. 19, 1990, abandoned.

[51] Int. Cl.$^5$ .................... C07D 417/04; G01N 37/00
[52] U.S. Cl. ........................ 428/71; 548/193; 548/194; 548/198
[58] Field of Search .............. 548/193, 194, 198; 424/701

[56] References Cited

U.S. PATENT DOCUMENTS 3,957,514  5/1976  Adir ..................................... 548/198

FOREIGN PATENT DOCUMENTS 0190740  8/1986  European Pat. Off. .
0239931  3/1987  European Pat. Off. .
3247894  6/1984  Fed. Rep. of Germany .

OTHER PUBLICATIONS

Die Pharmazie, vol. 34, No. 12, 1979, pp. 790–794; S. Johne et al: Compound 3, p. 792, Tables 2 and 3.
Chemical Abstracts, vol. 95, No. 19, Nov. 9, 1981, Abstract No. 95:169190j.
Patent Abstracts of Japan, vol. 9, No. 211 (C-300) (1934) Aug. 29, 1985.

*Primary Examiner*—Robert Gerstl
*Attorney, Agent, or Firm*—Andrew L. Klawitter; Jerome L. Jeffers

[57] ABSTRACT

2-Thiazolyl tetrazolium salt compounds characterized by a reflectance spectrum exhibiting an extended plateau above about 600–650 nm. Such compounds are useful as chromogenic indicators for reducing substances such as NADH. The reflectance plateau confers improved accuracy to analytical assays, particularly for the determination of analytes of medical diagnostic significance, in which a colorimetric response on a reagent carrier matrix is measured by reflectance.

13 Claims, 9 Drawing Sheets

SUBSTITUTED 2-THIAZOLYL TETRAZOLIUM SALT INDICATORS

This is a continuation, of application Ser. No. 585,650, filed Sep. 19, 1990, now abandoned.

BACKGROUND OF THE INVENTION

The present invention relates to chromogenic tetrazolium salt indicator compounds useful in the determination of reducing substances, particularly nicotinamide adenine dinucleotide (NADH).

Tetrazolium salts are well known as chromogenic indicators responsive to reducing substances. Upon reduction, tetrazolium salts are converted into formazan dye products. These indicators have found use in a wide variety of fields, particularly the medical diagnostic field where they have been applied to, among others, cell staining and the determination of analytes in body fluids such as urine, milk, serum, and plasma. Commonly, the determination of body fluid analytes involves an AND-dependent enzymatic reaction in which NADH is formed as a function of the amount of analyte present in the sample tested. The amount of NADH generated can then be determined by the reductive conversion of an appropriate tetrazolium salt indicator to its formazan dye product.

Within the field of medical diagnostic tests, tetrazolium salt indicators are useful in a variety of different product types. One particular type is the reagent strip. This product is a solid state device comprising a paper or other porous carrier matrix which is impregnated or otherwise incorporated with chemical reagents responsive to a particular analyte, for example, glucose or cholesterol. The incorporated reagent system includes a chromogenic indicator which develops color, or changes color, as a function of the amount of analyte in a sample applied to the matrix. The resulting colorimetric response can be observed visually to give qualitative or semi-quantitative readings. Quantitative results can be obtained by reading the reflectance of the matrix surface at one or more defined wavelengths with an appropriate instrument (reflectance meter).

There is a recognized need to develop tetrazolium indicators having strong absorbance at wavelengths longer than the absorbances of major interferants that can be present in the test sample. For instance, interference from hemoglobin coloration is a particular concern where the sample is whole blood. Indicators having significant absorption above about 640 nm are required in order to substantially overcome hemoglobin interference. The commonly used tetrazolium salt indicators are 2-(4-iodophenyl)-3-(4-nitrophenyl)-5-phenyltetrazolium chloride (INT), 3-(4,5-dimethylthiazol-2-yl)-2,5-diphenyltetrazolium chloride (MTT), and 2,2',5,5'-tetraphenyl-3,3'-(3,3'-dimethoxy-4,4-diphenylene) ditetrazolium chloride (NBT). These compounds show maximum absorption (UVmax) in the range of 465–605 nm.

Another shortcoming of the conventionally used prior art tetrazolium salt indicators relates to the evolution of the instrumentation used to measure their colorimetric response. Rapid advancements are being made in developing smaller, less expensive reflectance meters. One of the more costly components of such meters is the optical system which comprises a light source, a filter or other spectral element for selecting or limiting the wavelength of incident or reflect light, and a sensor. Significant cost savings could be realized by eliminating or combining functions of the optical system elements or by using less expensive components, e.g., LEDs as illuminating light sources. However, commercially available LEDs emit light having a center wavelength that can vary significantly due to manufacturing variances and temperature dependence. The conventionally used tetrazolium salt indicators INT, MTT, and NBT have reflectance spectra which are strongly sloped in the region above their UVmax. Accordingly, without individually calibrating both each instrument, to account for manufacturing variability in the LED, and each test run, to account for variance due to temperature, large errors can be introduced to the assay result.

The following are representative of the prior art teachings concerning the use of various tetrazolium salts in colorimetric analysis. Tanaka et al, Japanese Kokai Tokkyo Koho JP 61000084 (Chem. Abst. 104:203469y) describes the detection of glucose using a formazan chelate obtained by the reduction of 2-(2-benzothiazolyl)-3-(carboxy-phenyl)-5-phenyl-2H-tetrazolium halide in the presence of nickel (II). Limbach et al, German DE 3,247,894 (Chem. Abst. 101:125929v) relates to the use of INT in glucose assays. Rittersdorf et al, German DE 2,147,466 describes the use of seven 2-(2-benzothiazolyl)-3-phenyl-5-(4-[trimethylammonio]phenyl) tetrazolium salts in the determination of reducing substances such as reducing sugars, ascorbic acid, and ketosteroids.

The variety of 2-thiazolyl tetrazolium salts and/or their corresponding formazans known in the literature are represented by the following. Serebryakova et al, Khim. Geterotsikl. Soedin. 10:1403-1405 (1970) describe the synthesis and chromatic properties of benzothiazolyl-3-phenyl (methyl)-5-p-nitro(dimethylamino)-phenylformazans. The authors state that both an electron-withdrawing nitro group at the para-position of the 5-phenyl and a benzothiazolyl group at the 1-position provides a bathochromic shift. Lipunova et al, Khim. Geterotsikl. Soedin. (1971) 831-835 compare the bathochromic effect of an 5-naphthyl or o-tolyl group on the visible spectrum of N-1-benzothiazolyl formazans. Johne et al, Pharmazie 34:790-794 (1979) describe the compounds 1-(4-methyl-5-carb-ethoxythiazol-2-yl-3-(3-pyridyl)-5-(2-carboxyphenylformazan and 1-(4-methyl-5-carbethoxythiazol-2-yl-3-(2-pyridyl)-5-(2-carboxyphenyl) formazan.

SUMMARY OF THE INVENTION

The present invention provides thiazolyl tetrazolium salts which upon reduction yield formazans having new and improved optical properties. The compounds of the present invention are of the general Formula A:

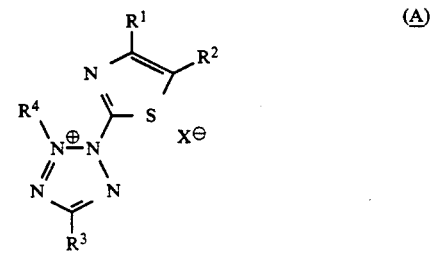

wherein (a) $R^1$ is carboxyl, carbalkoxy, carbaryloxy, carbamoyl, or cyano, and $R^2$ is alkyl or chloro, or (b) $R^1$ is alkyl or aryl, and $R^2$ is carboxyl, carbalkoxy, carbaryloxy, carbamoyl, or cyano, or (c) $R^1$ is di- or trifluoroalkyl wherein the fluoro substituents are on the carbon adjacent to the thiazolyl residue in the formula, and $R^2$ is chloro, wherein $R^3$ is selected from:

(a₁) residues of Formula B:

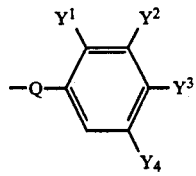

(B)

wherein Q is a bond or —CH±CH—, and wherein (i) $Y^1$ is alkoxy, aryloxy, alkyl, amido, alkylamido, arylamido, alkylthio, arylthio, halo, or hydrogen, $Y^2$ is alkoxy, aryloxy, alkyl, amido, alkylamido, arylamido, alkylthio, arylthio, amino, carbamoyl, carbalkoxy, carboxyl, cyano, halo, hydrogen, nitro, sulfo, sulfonamido, sulfamoyl, trialkylammonio, or ureido, $Y^3$ is alkoxy, aryloxy, alkyl, amido, alkylamido, arylamido, alkylthio, arylthio, amino, carbamoyl, carbalkoxy, carbaryloxy, carboxyl, cyano, halo, hydrogen, hydroxyl, nitro, sulfo, sulfonamido, sulfamoyl, trialkylammonio, or ureido, and $Y^4$ is alkoxy, halo, or hydrogen, or (ii) $Y^2$ and $Y^3$ together form methylenedioxy or imidazo and $Y^1$ and $Y^4$ are hydrogen, (b₁) 2, 3, or 4-pyridyl, (c₁) 2 or 3-thienyl, and (d₁) 2 or 3-furanyl;

wherein $R^4$ is selected from:

(a₂) residues of Formula C:

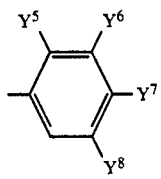

(C)

wherein $Y^5$ is alkoxy, aryloxy, alkyl, amido, alkylamido, arylamido, alkylthio, arylthio, halo, hydrogen, nitro, or ureido, $Y^6$ is alkoxy, aryloxy, alkyl, amido, alkylamido, alkylthio, arylthio, carbamoyl, carbalkoxy, carboxyl, cyano, halo, hydrogen, nitro, sulfo, sulfonamido, sulfamoyl, trialkylammonio, or ureido, $Y^7$ is alkoxy, aryloxy, amido, alkylamido, arylamido, alkylthio, arylthio, carbamoyl, carbalkoxy, carbaryloxy, carboxyl, cyano, hydrogen, hydroxyl, nitro, phenylazo, sulfo, sulfonamido, sulfamoyl, or ureido, and $Y^8$ is alkoxy, aryloxy, alkyl, halo, hydrogen or nitro, (b₂) residues of Formula D:

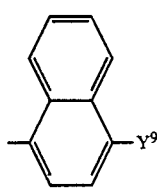

(D)

wherein $Y^9$ is alkoxy, aryloxy, alkyl, amido, alkylamido, arylamido, alkylthio, arylthio, carbamoyl, carbalkoxy, carboxyl, cyano, halo, hydrogen, nitro, phenylsulfo, sulfonamido, sulfo, sulfonamido, sulfamoyl, trialkylammonio, or ureido, (c₂) 2, 4, 6, or 8-quinolyl, or 2-methylquinolyl, and (d₂) anthranyl; and wherein X is a counteranion.

The present compounds are characterized by an absorption spectrum exhibiting an extended plateau above about 600 nm, preferably above about 650. Such absorption plateau confers improved accuracy to reflectance read reagent strip analytical assays, particularly where the optical measurement system has a variable central wavelength.

DESCRIPTION OF THE PREFERREd EMBODIMENTS

Figure 1:
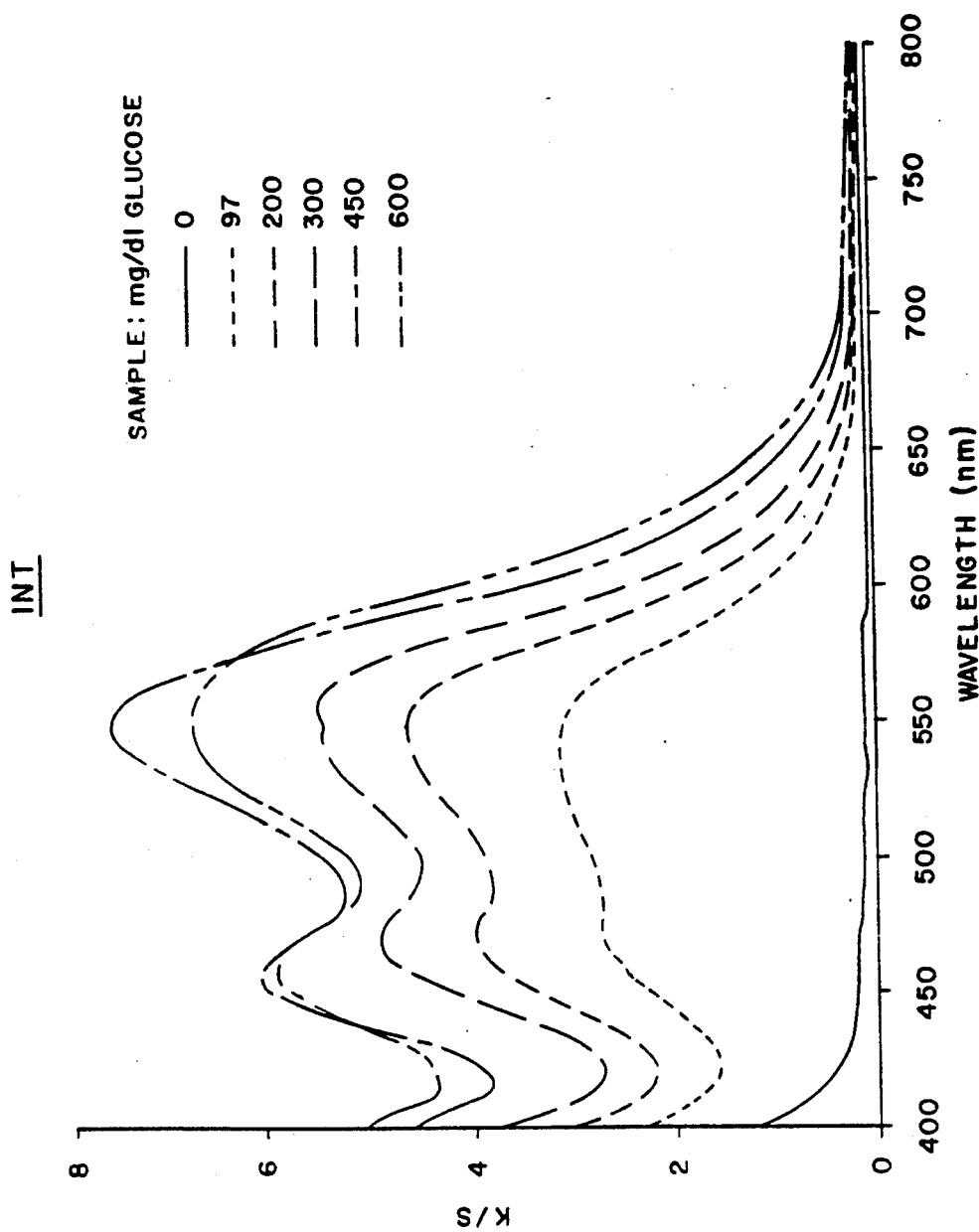
FIGS. 1–4 show the reflectance spectra of the formazans produced upon reduction of the prior art tetrazolium salts INT, MTT, NBT, and 2-(benzothiazol-2-yl)-3-(1-naphthyl)-5-phenyl tetrazolium salt (USSR) at various concentrations of glucose.

The following definitions shall apply to the subject disclosure:

"$C_{1-4}$"—used to limit a residue, e.g., $C_{1-4}$ alkyl, to those forms which contain between 1 and 4 relevant atoms, e.g., carbon atoms, inclusive.

"Alkyl"—linear and branched hydrocarbon residues of the general formula $C_nH_{2n+1}$, preferably "lower alkyl" such as the $C_{1-4}$ alkyls of methyl, ethyl, n-propyl, iso-propyl, n-butyl, iso-butyl, and tert-butyl, as well as higher alkyls such as n-pentyl, n-hexyl, and the like.

"Alkoxy"—the residue —OR wherein R is alkyl.

"Alkylamido"—the residue —NRC(=O)R' wherein R and R', same or different, are alkyl.

"Alkylthio"—the residue —SR wherein R is alkyl.

"Amido"—the residue —NHC(=O)H.

"Amino"—the residue —NRR' wherein R and R', same or different, are hydrogen or alkyl.

"Aryl"—organic residues derived from an aromatic carbocyclic or heterocyclic ring or ring system by removal of a hydrogen atom attached to such ring or ring system, e.g., phenyl, naphthyl, pyridyl, oxazolyl, quinolyl, thiazolyl, thienyl, furanyl, and the like.

"Arylamido"—the residue —NRC(=O)R' wherein R and R', same or different, are aryl.

"Aryloxy"—the residue —OR wherein R is aryl.

"Arylthio"—the residue —SR wherein R is aryl.

"Carbalkoxy"—the residue —C(=O)OR wherein R is alkyl.

"Carbaryloxy"—the residue —C(=O)OR wherein R is aryl.

"Carbamoyl"—the residue —C(=O)NRR' wherein R and R', same or different, are hydrogen or alkyl.

"Carboxyl"—the residue —C(=O)OH.

"Halo"—fluoro, chloro, and bromo.

"Imidazo"—the divalent residue —N=CH—NH—.

"Methylenedioxy"—the divalent residue of the formula —O—CH₂—O—.

"Phenylazo"—the residue —N=N-phenyl.

"Styryl"—the residue —CH=CH—R wherein R is aryl.

"Sulfo"—the residue —SO₃.

"Sulfamido"—the residue —NRSO$_2$R' wherein R and R', same or different, are alkyl, aryl, or hydrogen.

"Sulfamoyl"—the residue —SO$_2$NRR' wherein R and R', same or different, are alkyl, aryl, or hydrogen.

"Trialkylammonio"—the residue —NR$_3$+ wherein R is alkyl.

"Ureido"—the residue —NRC(=O)NR' wherein R and R', same or different, are alkyl, aryl, or hydrogen.

It will be understood that, unless otherwise specifically stated, it is intended that the use of the above terms in the case of residues that can be substituted or unsubstituted, e.g., alkyl, aryl, phenylaro, and styryl, shall include the reasonably substituted forms of such residues as well as their unsubstituted forms. Reasonable substitutions which will produce useful compounds of the present invention will be evident to one of ordinary skill in the art, and will include such substituents, without limitation, as alkoxy, amino, alkylthio, carbalkoxy, carboxy, hydroxy, sulfo, and sulfamoyl, just to name a few.

Preferred R$^1$ and R$^2$ Residues

From the standpoints of synthesis and reflectance spectrum properties of the formazan, preferable compounds are those wherein (a) R$^1$ is carb(C$_{1-4}$)alkoxy and R$^2$ is C$_{1-4}$ alkyl or chloro, or (b) R$^1$ is C$_{1-4}$ alkyl or phenyl, and R$^2$ is carb(C$_{1-4}$)alkoxy, or (c) R$^1$ is di- or tri-fluoromethyl and R$^2$ is chloro. Most preferred are those compounds wherein R$^1$ is di- or trifluoromethyl and R$^2$ is chloro.

Preferred R$^3$ and R$^4$ Residues

From the standpoints of synthesis and reflectance spectrum properties of the formazan, R$^3$ will preferably be selected from:

(a$_1$) residues of Formula E:

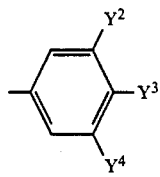 (E)

wherein
(i) Y$^2$, Y$^3$, and Y$^4$ are each C$_{1-4}$ alkoxy,
(ii) Y$^4$ is hydrogen and Y$^2$ and Y$^3$ are both C$_{1-4}$ alkoxy or together form methylenedioxy, or
(iii) Y$^2$ and Y$^4$ are both hydrogen and Y$^3$ is C$_{1-4}$ alkoxy, C$_{1-4}$ alkyl, C$_{1-4}$ alkylamido, alkylthio, C$_{1-4}$ alkylthio, carbamoyl, carb(C$_{1-4}$)alkoxy, carboxyl, cyano, halo, hydrogen, nitro, tri(C$_{1-4}$)alkylammonio, or ureido, and
(b$_1$) 2 or 3-thienyl.

Based on the properties and synthesis of compounds that have been prepared, it is most preferred that R$^3$ be selected from:
3,4,5-trimethoxyphenyl,
3,4-dimethoxyphenyl,
3,4-methylenedioxyphenyl,
4-methoxyphenyl,
4-acetamidophenyl,
4-methylthiophenyl,
4-phenyl,
4-halophenyl,
4-cyanophenyl,
4-nitrophenyl,
2-thienyl, and
3-thienyl.

The preferred R$^4$ residues are:
(a$_2$) residues of Formula C, supra, wherein
(i) Y$^5$ is hydrogen and each of Y$^6$, Y$^7$, and Y$^8$ is C$_{1-4}$ alkoxy,
(ii) Y$^5$ and Y$^8$ are both hydrogen and Y$^6$ and Y$^7$ are both C$_{1-4}$ alkoxy or together form methylenedioxy,
(iii) Y$^5$, Y$^6$ and Y$^8$ are each hydrogen and Y$^7$ is C$_{1-4}$ alkoxy, C$_{1-4}$ alkylamido, C$_{1-4}$ alkylthio, benzamido, carbamoyl, carb(C$_{1-4}$)alkoxy, carboxyl, cyano, hydroxyl, nitro, phenylazo, sulfo, sulfonamido, sulfamoyl, or ureido,
(iv) Y$^5$ is alkoxy or alkyl, Y$^6$ and Y$^8$ are both hydrogen, and Y$^7$ is C$_{1-4}$ alkoxy, C$_{1-4}$ alkylamido, C$_{1-4}$ alkylthio, benzamido, carbamoyl, carb(C$_{1-4}$)alkoxy, carboxyl phenylazo, or ureido,
(v) Y$^5$ and Y$^8$ are C$_{1-4}$ alkoxy, or
(vi) Y$^5$ and Y$^8$ are C$_{1-4}$ alkoxy and Y$^7$ is C$_{1-4}$ alkylamido or benzamido;
(b$_2$) residues of Formula D, supra, wherein Y$^9$ is C$_{1-4}$ alkoxy, C$_{1-4}$ alkyl, C$_{1-4}$ alkylamido, C$_{1-4}$ alkylthio, benzamido, cyano, halo, hydrogen, nitro, sulfo, sulfonamido, or ureido, and
(c$_2$) 8-quinolyl.

Based on the properties and synthesis of compounds that have been prepared, it is most preferred that R$^4$ be selected from:
3,4,5-trimethoxyphenyl,
3,4-dimethoxyphenyl,
2,4-dimethoxyphenyl,
3,4-methylenedioxyphenyl,
4-methoxyphenyl,
4-acetamidophenyl,
4-methylthiophenyl,
4-carboxyphenyl,
4-nitrophenyl,
2-methoxyphenyl,
2-methoxy-4-carboxyphenyl,
2,5-dimethoxyphenyl,
2,5-dimethoxyphenyl-4-benzamidophenyl,
1-naphthyl,
4-nitro-1-naphthyl,
4-methoxy-1-naphthyl,
8-quinolyl,
2-methyl-4-carboxyphenyl,
4-carbmethoxyphenyl,
4-cyanophenyl, and
4-cyano-1-naphthyl.

Counteranion

The selection of the counteranion will be based primarily on considerations of stability and solubility of the particular tetrazolium salt of interest. In general, one can select from such counteranions as the inorganic anions chloride, bromide, iodide, nitrate, fluroborate, perchlorate, and sulfate, as well as organic anions such as acetate, oxalate, tartrate, and aryl sulfonates (benzene sulfonate, tosylate).

Synthetic Methods

Tetrazolium salts are prepared by methods well known in the literature (Hooper, W. D., Rev. Pure and Appl. Chem., 1969, 19, 221; Putter, R., in Methoden der Organischen Chemie, Houben-Weyl-Muller ed., Thieme Verlag: Stuttgart, 1965, Bd. 10/3, p. 633; Nineham, A. W. Chem. Rev., 1955, pp. 355–483). In general, the tetrazolium salts of the present invention are prepared by first reacting a 2-hydrazinothiazole with an aldehyde and then treating the resulting hydrazone with a diazotized aniline. The resulting formazan is then oxidized to the tetrazolium salt by well known methods. Consequently, the synthesis involves three principal starting materials, the aldehyde, the aniline, and the 2-hydrazinothiazole.

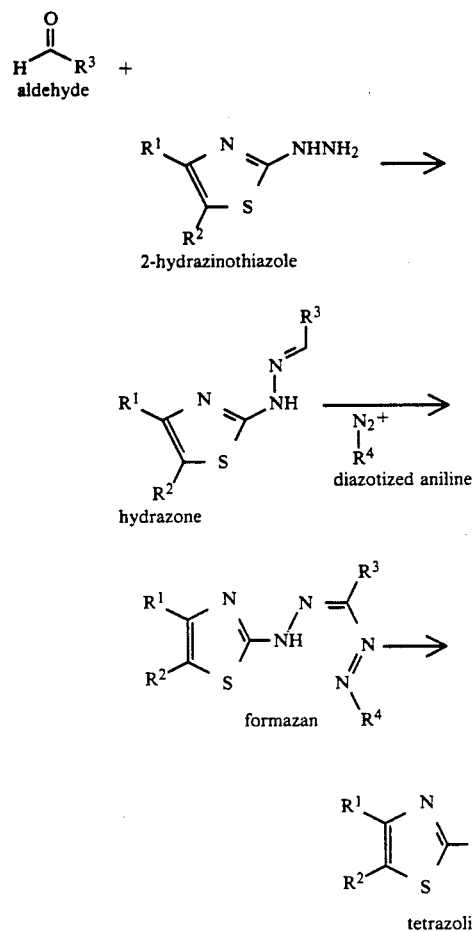

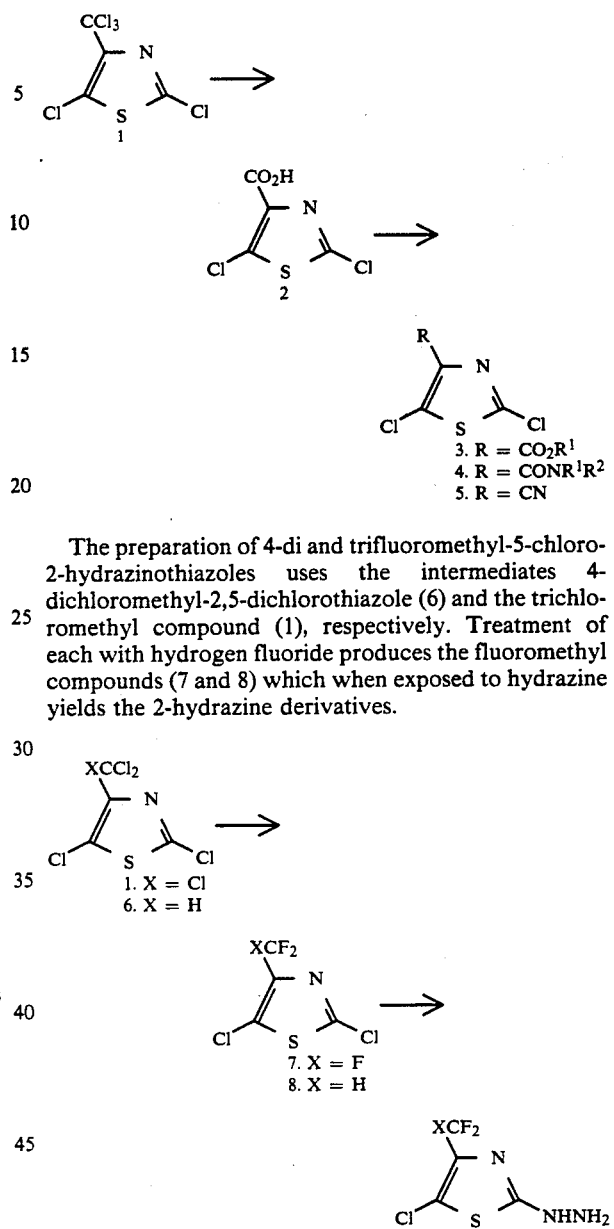

The preparation of 4-di and trifluoromethyl-5-chloro-2-hydrazinothiazoles uses the intermediates 4-dichloromethyl-2,5-dichlorothiazole (6) and the trichloromethyl compound (1), respectively. Treatment of each with hydrogen fluoride produces the fluoromethyl compounds (7 and 8) which when exposed to hydrazine yields the 2-hydrazine derivatives.

Preparation of 2-hydrazinothiazoles

Chlorination of the known 2-chloro-4-methylthiazole (J. Chem. Soc. 1919, pp. 1071–1090) at 100° C. leads primarily to the 2,5-dichloro-4-dichloromethylthiazole (6) and at 160° C., 2,5-dichloro-4-trichloromethylthiazole (1).

4-Carbalkoxy-5-chlorothiazole is prepared by hydrolysis of 2,5-dichloro-4-trichloromethylthiazole (1) to yield the carboxylic acid (2) (European Patent Publication No. 348,735). Treatment with reagents such as thionyl chloride yield the acid chloride which reacts with alcohols or amines to yield 4-carbalkoxy (3) or N-alkylcarbamoyl (4) thiazoles. Dehydration of 4-carbamoyl-2,5-dichlorothiazole is accomplished by methods well known in the literature to yield 4-cyano-2,5-dichlorothiazole (5). (March, J. Advanced Organic Chemistry Third Edition; John Wiley and Sons: New York, 1985, pp. 932–933).

The thiazoles, 4-alkyl or aryl-5-carbalkoxy, amido, or cyano-2-substituted thiazoles are prepared by halogenating the appropriate β-ketoester, amide or nitrile and reacting it with thiourea or thiosemicarbazone (Metzger, J. V., in Comprehensive Heterocyclic Chemistry, Katritzky, A. R., Rees, C. W., ed.; Peragamon: New York, 1985; vol. 6, Part 4 p. 297; Beyer, H., Bulka, E., Z. Chem., 1962, 2, 321–328).

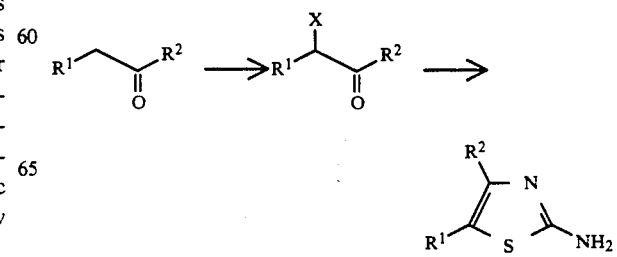

$R^1 =\ CO_2R^3$
$CONR^3R^4$
CN, aryl, alkyl
$R^2 =$ alkyl, aryl

Preparation of aldehydes

The aldehydes are obtained from commercial sources or can be prepared by methods familiar to one of ordinary skill in the art.

For instance, aldehydes may be prepared by benzylic oxidation of an arylmethane (March, J., Advances Organic Chemistry Third Edition; John Wiley and Sons: New York, 1985; p. 1079), reduction of an aryl acid chloride (Ibid. p. 396) or aryl acid derivative, [Larock, R. C., Comprehensive Organic Transformations; VCH: New York, 1989; pp. 604–605).

Aryl halides may also be used to synthesize aldehydes. In this method, a transmetallation reaction produces an arylmetallic species which can be treated with a variety of reagents, such as dimethylformamide, to produce the aldehyde (ibid, p. 681–683).

The aforementioned aryl aldehydes, acids, methanes, and halides, may be derivatized with a variety of functional groups prior to their transformation into tetrazolium salts. This may be accomplished by aromatic nucleophilic substitution (March, J., Advanced Organic Chemistry Third Edition; John Wiley and Sons: New York, 1985; pp. 576–607), aromatic electrophilic substitution (ibid., pp. 447–511) or heteroatom-directed metallation reactions (Gschwend, H. W., Rodriguez, H. R., in Organic Reactions, John Wiley and Sons: New York, 1979; Vol. 26, 1).

In cases where the aldehyde piece of the tetrazolium salt contains a phenol or amine, the groups must be protected so that there is not a reaction between these and the diazotized aniline or oxidizing reagent used to prepare the tetrazolium salt.

This can be accomplished by protecting a hydroxyaryl aldehyde as an acetate, performing the reaction sequence to make the formazan, and then hydrolyzing the acetate at pH 10. Acidification to pH 5 and then filtration produces the desired formazan.

Where the resulting phenol formazan reacts with oxidizing agent in the tetrazolium salt preparation, the phenol may be protected by an acid labile group such as dihydropyran (Greene, T. W., Protective Groups in Organic Synthesis, John Wiley and sons: New York; 1981, pp. 87–113) and which is removed by stirring the tetrazolium salt in acidic conditions.

Similarly amines on the aldehyde piece must be protected to prevent their reaction. This is best accomplished by using an acid labile carbamate (ibid, pp. 218–247) which is later removed by stirring the tetrazolium salt under acidic conditions.

Preparation of Aryl Amines

Aryl amines may be prepared by reduction of the corresponding nitro or azide compound (Larock, P. C., Comprehensive Organic Transformations; VCH: New York, 1989; pp. 412–415 or 409–410), reaction between an arylmetallic compound and an electrophilic nitrogen reagent, (ibid., pp. 399–400), or rearrangement of acyl azides or oxidized amides (ibid., pp. 431–432).

As in the aldehyde case, electrophilic and nucleophilic aromatic substitution can be used to introduce different functional groups into the aryl amine or synthetic precursor.

Use of the Compounds

The principal use of the tetrazolium salt compounds of the present invention are as chromogenic indicators for detecting reducing substances. In particular, the present compounds are advantageous in the detection of NADH. As such, since NADH is produced in enzyme-catalyzed detection reactions specific for various biochemical substances, the present compounds are particularly useful in medical diagnostic tests. However, in general other reducing substances can also be detected, such as hydrogen sulfide gas, diborane, arsenic hydride, or phosphorus hydride.

The present compounds have been particularly found to exhibit an extended plateau in their reflectance spectrum above about 600 nm. The most preferred compounds of the present invention have a plateau above about 650 nm (i.e., the flatest about 50 nm wide portion begins between 640 and 600 nm). Such a reflectance plateau confers improved accuracy to analytical tests based on the measurement of reflectance from a reagent strip.

Reagent strips are known in the art as analytical devices comprising a solid carrier matrix incorporated with a test composition that produces a color change in response to contact with a liquid test sample containing the analyte of interest. Such test composition, in the case of the present invention, comprises (a) a reagent or reagents which react with the analyte to produce a reducing substance, and (b) a 2-thiazolyl tetrazolium salt as described herein which is reducable by such reducing substance to produce a chromogenic formazan dye product. The color response of such reagent strips can be observed visually to give semi-quantitative values, however, quantitative results are obtained by measuring the reflectance of the carrier matrix at a predetermined wavelength. Such measurements involve irradiating the reacted carrier matrix with a light source and sensing the reflectance of the carrier matrix by measuring reflected light with a detector element.

The finding of tetrazolium salt indicators having a reflectance plateau is used to particular advantage where reflectance from a reagent strip is read using an instrument which is subject to variability in the central wavelength of its optical system (the combination of light source, detector element, spectral control elements, e.g., filters), and other components). Variability in the central wavelength of the optical system can be caused by a variety of factors, for example, variability in the central wavelength of the principal spectral control element such as the illuminating light source or filters. For instance, where light emitting diodes (LEDs) are used as the light source, the wavelength of emitted light will typically vary ±4 nm within an instrument, and up to ±8 nm between LEDs in different instruments, due to manufacturing variability. Moreover, LEDs are suceptible to variable central wavelength due to temperature effects as well. Where broad band light sources are used with filters to provide spectral control of the central wavelength, variability within an instrument is typically under 1 nm, however, between instrument variability can be as high as ±6 nm. Thus, the present invention is applicable in those situations where the central wavelength of the light reaching the detector element in the instrument is susceptible to variations in the range of about ±5 nm.

In the making of a reagent strip for use in the present invention, selection of the carrier matrix, the test reagents which react with analyte to produce the reducing substance, and the method by which such reagents and the tetrazolium indicator are incorporated with the carrier matrix are matters well known in the art of reagent strips. For the sake of reciting just a few examples, typical carrier matrices are porous and absorbent paper, cloth, glass fiber filters, polymeric membranes and films, and the like. Incorporation methods include impregation of a formed carrier matrix with a solution, suspension, or other liquid form of the test composition, in one or more steps, followed by drying of the matrix; formation of a matrix in the presence of one or more of the components of the test composition, e.g., by casting or layering solutions of film or membrane forming formulations.

The present invention will now be illustrated, but is not intended to be limited by, the following examples.

EXAMPLES

A. Compound Synthesis

Hydrazone Preparations

Preparation of Aryl Aldehyde 4-di- or Trifluoromethyl-5-chlorothiazol-2-yl Hydrazones A slurry of 25 mmole of the appropriate aldehyde and 25 mmole of the appropriate hydrazine in 125 mL of absolute ethanol, is refluxed for 3 hours. Water is removed with 3A molecular sieves in a Soxhlet extractor. The mixture is cooled to room temperature and then filtered to yield the hydrazone.

Preparation of Aryl Aldehyde 4-alkyl or Aryl-5-carbalkoxy-thiazol-2-yl Hydrazones Hydrazones derived from 4-alkyl or aryl-5-carboalkoxythiazoles were prepared by refluxing for one hour a 0.3 m/L of a 3-alkyl or aryl-3-oxo-2-chloropropionic ester with the same concentration of the appropriate thiosemicarbazone in ethanol as described by H. Beyer and E. Bulka in Z. Chem., 2, 321(1962). After cooling to room temperature, the mixture was filtered to produce the hydrazone.

Preparation of Aryl Aldehyde 4-carbalkoxy-5-alkyl or Aryl Thiazol-2-yl Hydrazones Hydrazones derived from 4-carbalkoxy-5-alkyl or aryl-5-thiazoles were prepared from a 1-chloro-1-carbalkoxy-2-alkyl or aryl oxirane and the appropriate thiosemicarbazone. The required oxirane may be prepared by the method of A. Takada, et al., in Bull. Soc. Chem. Jpn., 43, 2997(1970). A solution of 30 mmol of the oxirane and 30 mmol of the thiosemicarboazone in 100 mL of ethanol was prepared and refluxed for 1 hour. The mixture was allowed to cool and then was filtered to produce the hydrazone.

Formazan Preparation

The diazonium salt is first prepared by cooling a slurry or solution of 8.5 mmol of the amine in 60 mL of N HCl to 5° C. Sodium nitrite (0.70 g, 10.15 mmol) in 5 mL of water is then added dropwise. After stirring for 30 minutes, the mixture added dropwise to a cold ($-25°$ C.) mixture of 8.5 mmol of the hydrazone in 120 mL of 1:1 (v/v) DMF-pyridine. The reaction is not allowed to warm beyond $-15°$ C. during the addition. The mixture is allowed to warm to room temperature while stirring for two hours. Filtration produces the formazan as a black solid. Impurities can be removed by repeated washing with methanol or refluxing the solid in methanol and filtering while hot.

Tetrazolium Salt Preparation

A slurry of 1.5 mmol of the formazan is stirred with 20 mL of acetic acid and 4 mL of isoamyl nitrite for a period of 16-48 hours. The mixture is then filtered to yield the tetrazolium salt. In cases where the salt does not precipitate, dilution with ether caused precipitation.

2,5-dichloro-4-dichloromethylthiazole

A vigorous stream of chlorine was entered into 5888 g (42.9 mol) 97.3% 2-chloro-4-methyl-thiazole (J. Chem. Soc. 1919, pp. 1071–1090), initially at 80° C., after the exothermic reaction slowly ended at 100° C. for about 100 hours. After cooling to room temperature and standing overnight, a crystalline precipitate formed of 2,5-dichloro-4-dichloromethylthiazole which was filtered off and dried on ceramic clay. Yield 3907 g (38.4% of theory.)

The fluid fraction of the chlorination mixture was subjected to fractionated distillation in a 2-meter filled column. The distillate obtained at 101° C. to 103° C./6 mbar crystallized to a large extent and then was dried on ceramic clay. Yield of 2,5-dichloro-4-dichloromethylthiazole by fractionated distillation : 2733 g (26.9% of theory.)

Total yield 6640 g (75.3% of theory). Mp. 42°–44° C. (recrystallized from petroleum ether.)

$^1$H—NMR (in CDCl$_3$): $\delta = 6.78$ ppm.

2,5-dichloro-4-trichloromethylthiazole

Chlorine gas was passed into a mixture of 1093 g (8.19 mol) 2-chloro-4-methylthiazole and 4 liter methylene chloride in a three-neck flask equipped with a stirrer, thermometer, reflux condenser and gas tube, starting at room temperature. After the exothermic reaction died out, the methylene chloride was distilled off under a slow temperature increase with continued introduction of chlorine; the melt was slowly heated to about 160° C. At about 160° C., mostly excess chlorine gas (recognizable by the slight greenish color of the escaping gas) was bubbled in until a gas chromatogram showed almost solely the desired compound 2,5-dichloro-4-trichloromethyl-thiazole. Total duration of chlorination 40 to 50 hours.

A crude distillation up to a head temperature of 150° C. at 14 mbar gave 2057 g ca. 95% pure 2,5-dichloro-4-trichloromethyl-thiazole, corresponding to a yield of 88% of theory in pure product. 2,5-dichloro-4-trichloromethyl-thiazole was obtained pure by fine distillation through a silver-coated, 220-cm filled column. Boiling point 123°–125° C. at 16 mbar.

2,5-dichloro-4-difluoromethylthiazole 1010 g (4.26 mol) 2,5-dichloro-4-dichloromethyl-thiazole were fluorinated with 1500 ml anhydrous hydrofluoric acid in a VA-autoclave at 145° C./25 bar. The forming hydrochloric acid was continually removed. Excess hydrofluoric acid was drawn off under vacuum at room temperature at the end of the reaction. The residue was added to ice water, taken up in dichloromethane, dried over sodium sulfate and distilled.

The yield was 753 g (86.6% of theory) 2,5-dichloro-4-difluoromethyl-thiazole bp. 74°–75° C./18 mbar; $n_D^{20} = 1.5171$.

2,5-dichloro-4-trifluoromethylthiazole 750 g (2.76 mol) 2,5-dichloro-4-trichloromethyl-thiazole were fluorinated with 1000 ml anhydrous hydrofluoric acid in a VA-autoclave at 130° C./19–20 bar. Formed HCl was continually removed. Excess hydrofluoric acid was drawn off under vacuum at toom temperature at the end of the reaction. The residue was poured on ice water, taken up in dichloromethane, dried over sodium sulfate and distilled.

The yield was 570 g (93% of theory) 2,5-dichloro-4-trifluoromethylthiazole; bp. 164° C.; $n_D^{20} = 1/4474$

5-chloro-2-hydrazino-4-trifluoromethylthiazole 75 g (1.5 mol) hydrazine hydrate were added to a mixture of 111 g (0.5 mol) 2,5-dichloro-4-trifluoromethylthiazole and 500 dioxan at such a rate that a reaction temperature of 25° C. was not exceeded. After further stirring for 20 hours at room temperature, the reaction mixture was stirred into 2.5 liter ice water; then one filtered off, washed the residue with water and dried.

The yield was 87.3 g (80.3% of theory) 5-chloro-2-hydrazino-4-trifluoromethyl-thiazole, mp. 136°–137° C.

5-chloro-2-hydrazino-4-difluoromethylthiazole

Similar to 5-chloro-2-hydrazino-4-trifluoromethyl-thiazole, one obtains from 2,5-dichloro-4-difluoromethylthiazole 5-chloro-2-hydrazino-4-difluoromethyl-thiazole in 51.3% yield. Mp. 132° C. (decomp.) (after recrystallization from much cyclohexane).

Smaller amounts of the compound can be sublimated at 70° C./0.1 mbar.

B. Preparation of Reagent Strips

Each indicator was impregnated into a reagent strip and tested with a solution containing a known quantity of glucose or cholesterol. The reagent strip consists of a polystyrene handle onto which a single reagent pad is attached. The reagent pad was 0.2×0.2″ square and contains reagents allowing for a color change which was instrumentally read when an aliquot of sample containing the appropriate analyte was applied. The dry-phase reagent pad is a solid support composed of cellulosic fibers or a nylon membrane as examples. The reagent pad was impregnated first with a solution of the tetrazolium salt of interest (0.08M/L) and detergent (9.3%) in a solvent such as methanol. The second solution impregnated into the reagent pad contains the following components:

| Glucose Strips | |
| --- | --- |
| Glucose Dehydrogenase (GDH) | 0.8 U/L |
| Diaphorase (DPH) | 0.8 U/L |
| NAD | 0.15 Mol/L |
| Detergent | 0.5% |
| Cholesterol Strips | |
| Cholesterol Dehydrogenase (CDH) | 0.3 U/L |
| Cholesterol Ester Hydrolase (CEH) | 0.6 U/L |
| Diaphorase | 0.3 U/L |
| NAD | 0.045 Mol/L |
| Pipes Buffer | 0.2 Mol/L |
| Detergent | 1% v/v |

About 0.01 ml of several test solutions (serum, plasma, aqueous) containing at least five different analyte concentrations between 0 and 33 mM/L was applied to the center of the dried reagent pad. After a lag time of about 60 seconds, the reflectance spectra of each indicator was measured at 5 nm increments over the wavelength range of 400 to 1000 nanometers.

C. Utility Data

Following is a table of spectral and other analytical data pertaining to various synthesized tetrazolium salts of the present invention. The compounds are organized, in order, by the form of their thiazolyl residue, then by their $R^4$ substituent and finally by their $R^3$ substituent. For example, the first compound presented is A.1.a) and is of the Formula A wherein $R^1$ is 4-difluoromethyl, $R^2$ is 5-chloro, $R^4$ is 4-nitrophenyl, and $R^3$ is 4-(2-(2-(2-ethoxy)ethoxy)ethoxy)phenyl; the second compound, A.1.b), has the same substitutions on the thiazolyl residue and the same $R^4$ substituent as compound A.1.a) but with $R^3$ being 4-(2-(2-(2-methoxy)ethoxy)ethoxy)phenyl; and so forth.

The reflectance spectrum of tetrazolium salts is understood to be dependent upon the environment in which they are observed or measured. For purposes of comparison between individual tetrazolium salts, the data below include a measurement of the relative flatness of the flatest portion of the reflectance spectrum at wavelengths greater than about 600 nm, which spectrum is generated using a glucose or cholesterol reagent strip prepared as described in Part B above. The relative flatness of the spectrum is expressed in the data in K/S units normalized for the level of analyte detected as defined below.

K/S is defined by the equation $$\frac{(1-R)^2}{2R}$$

wherein R is reflectance units. Percent change in K/S is the change, expressed as a percentage, over a 50 nm range divided by the average of the high and low K/S values over such range.

The plateau property of the present compounds shall be understood, for the purposes of this invention, as a percent change in reflectance spectrum (expressed in terms of K/S as defined in the paragraph above) of less than about 17% over a 30–50 nm wavelength span beginning at a wavelength above about 600 nm. The more preferable compounds exhibit a plateau having a percent change in K/S of less than an about 10%. Most preferred are those tetrazolium salt indicators exhibiting a percent change in K/S of about 5% or less over a 50 nm wavelength span. Compounds having a more sloped reflectance sprectrum are nonetheless preferred where the flatest portion is a wavelength above 650 nm, preferably above 675 nm.

Figure 2:
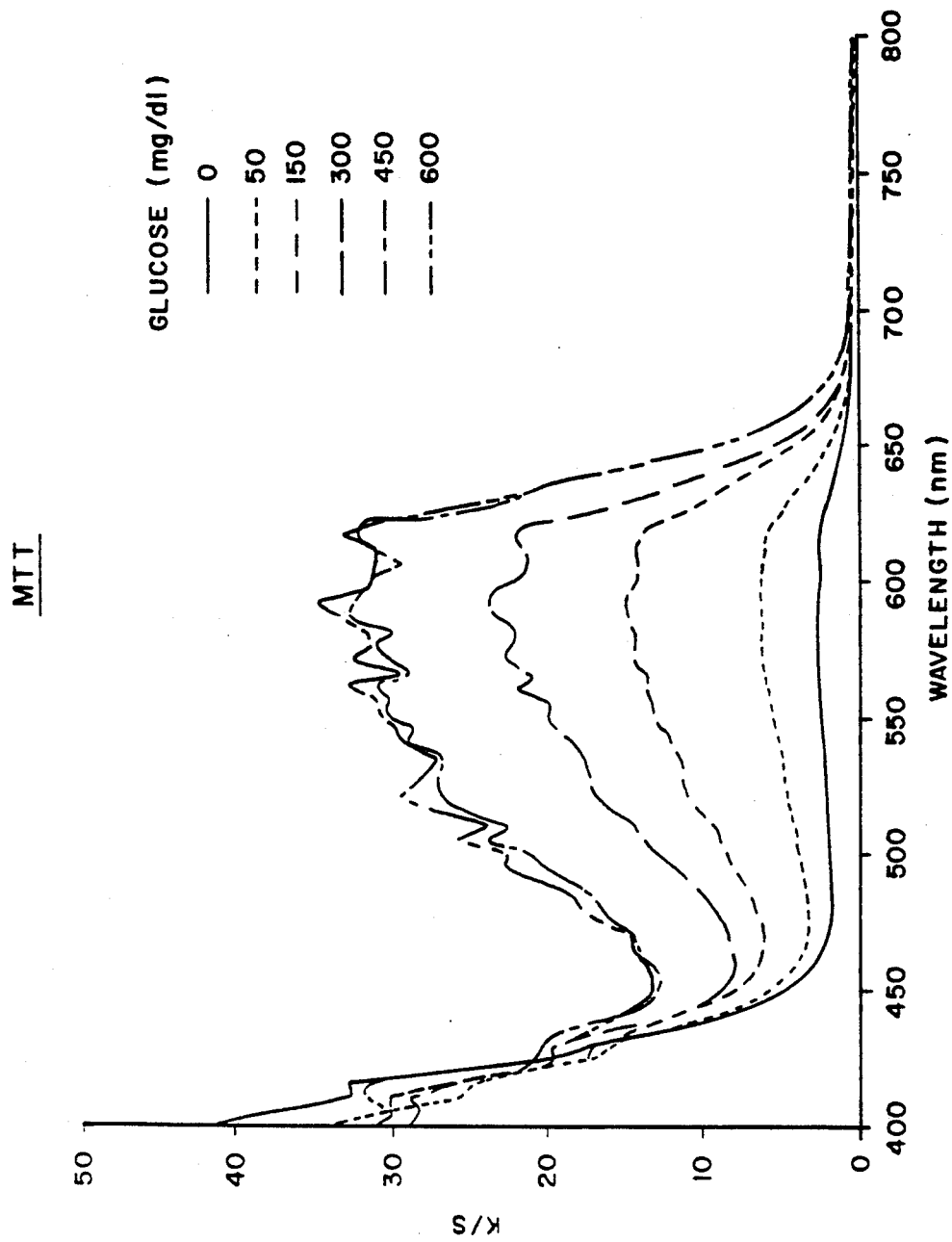
Figure 3:
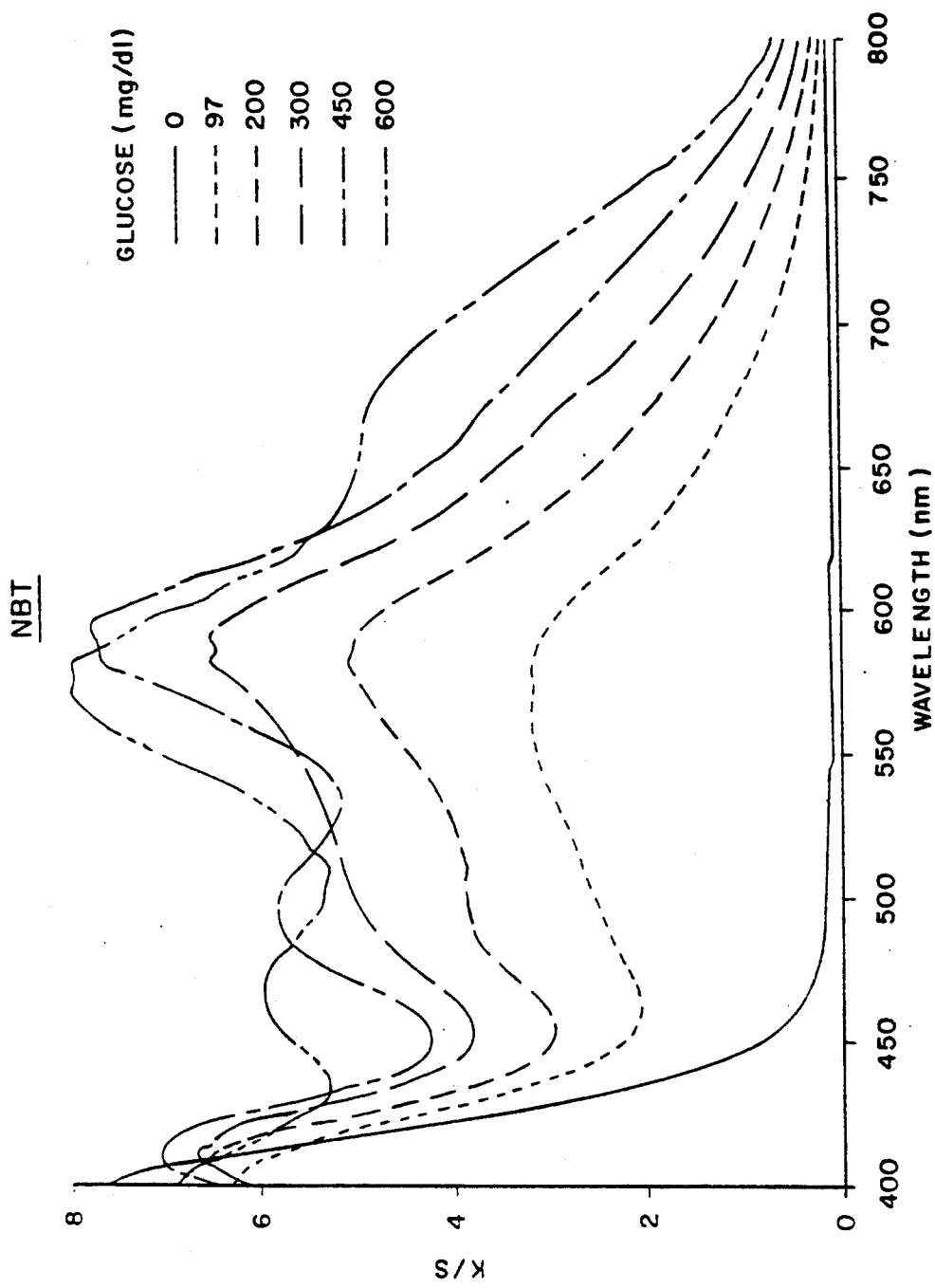
Figure 4:
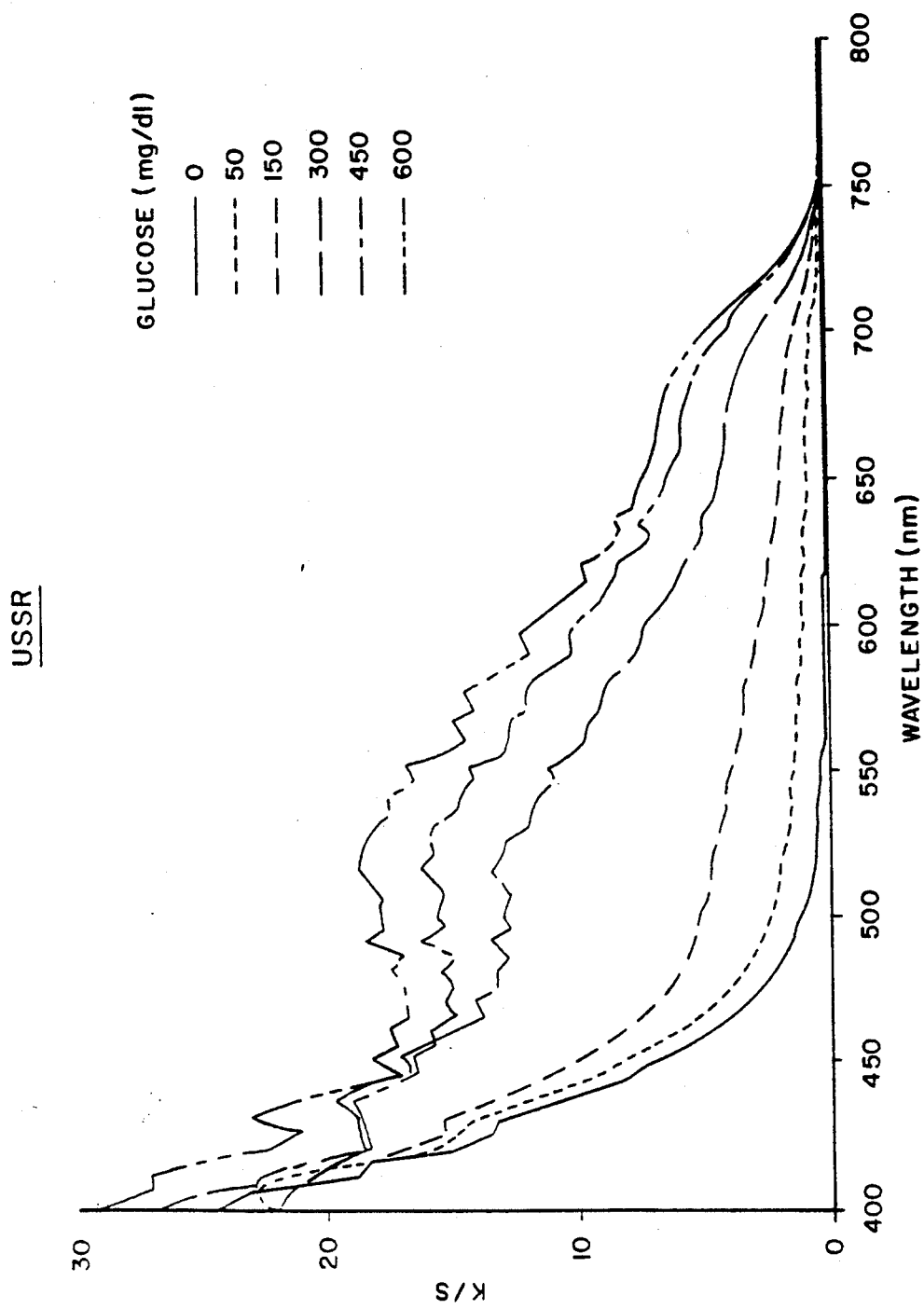
Figure 5:
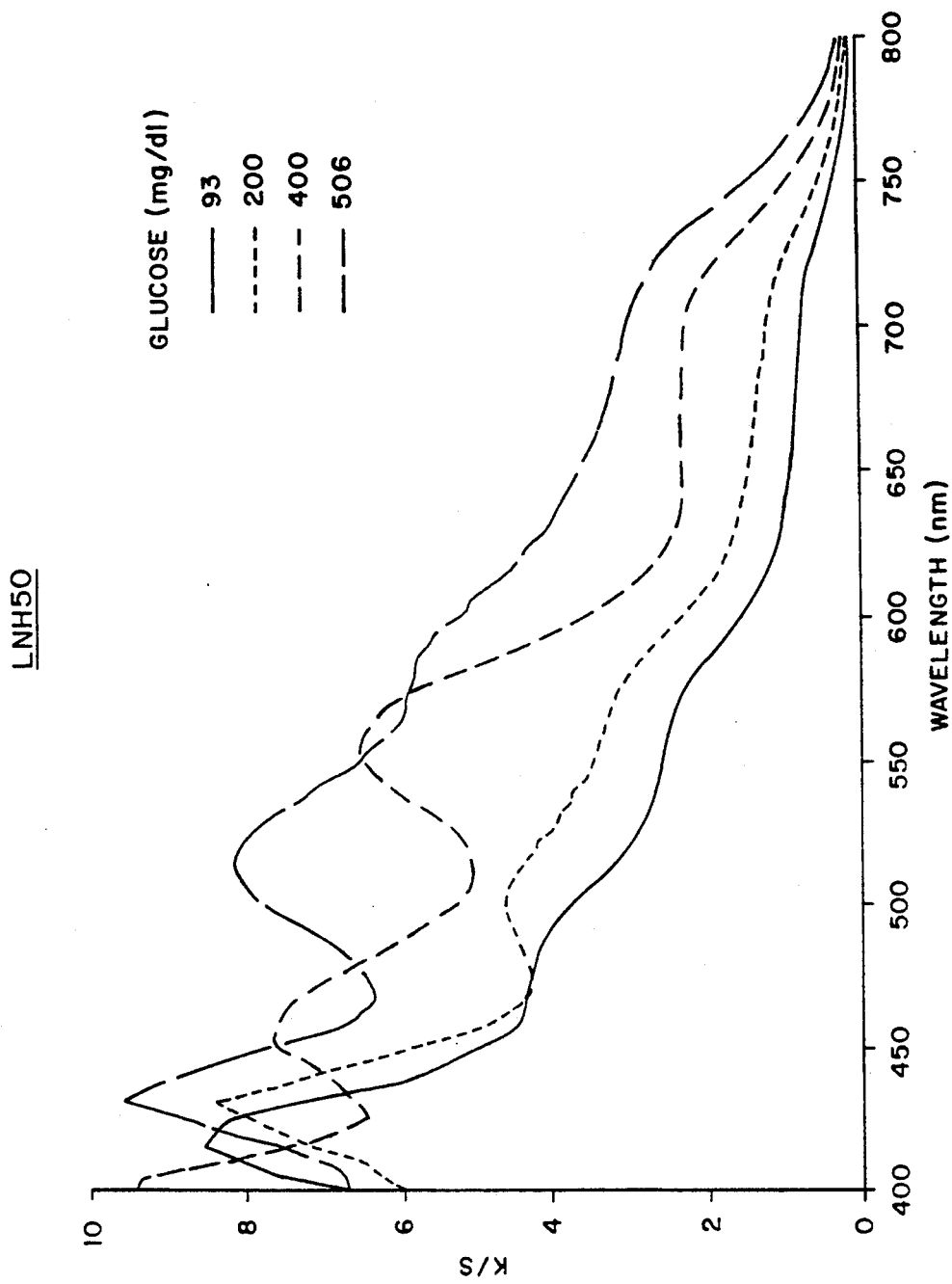
FIGS. 5–9 show the corresponding spectra for the formazans from particular indicator compounds of the present invention (see list at the beginning of the Table in the Examples section).
Figure 6:
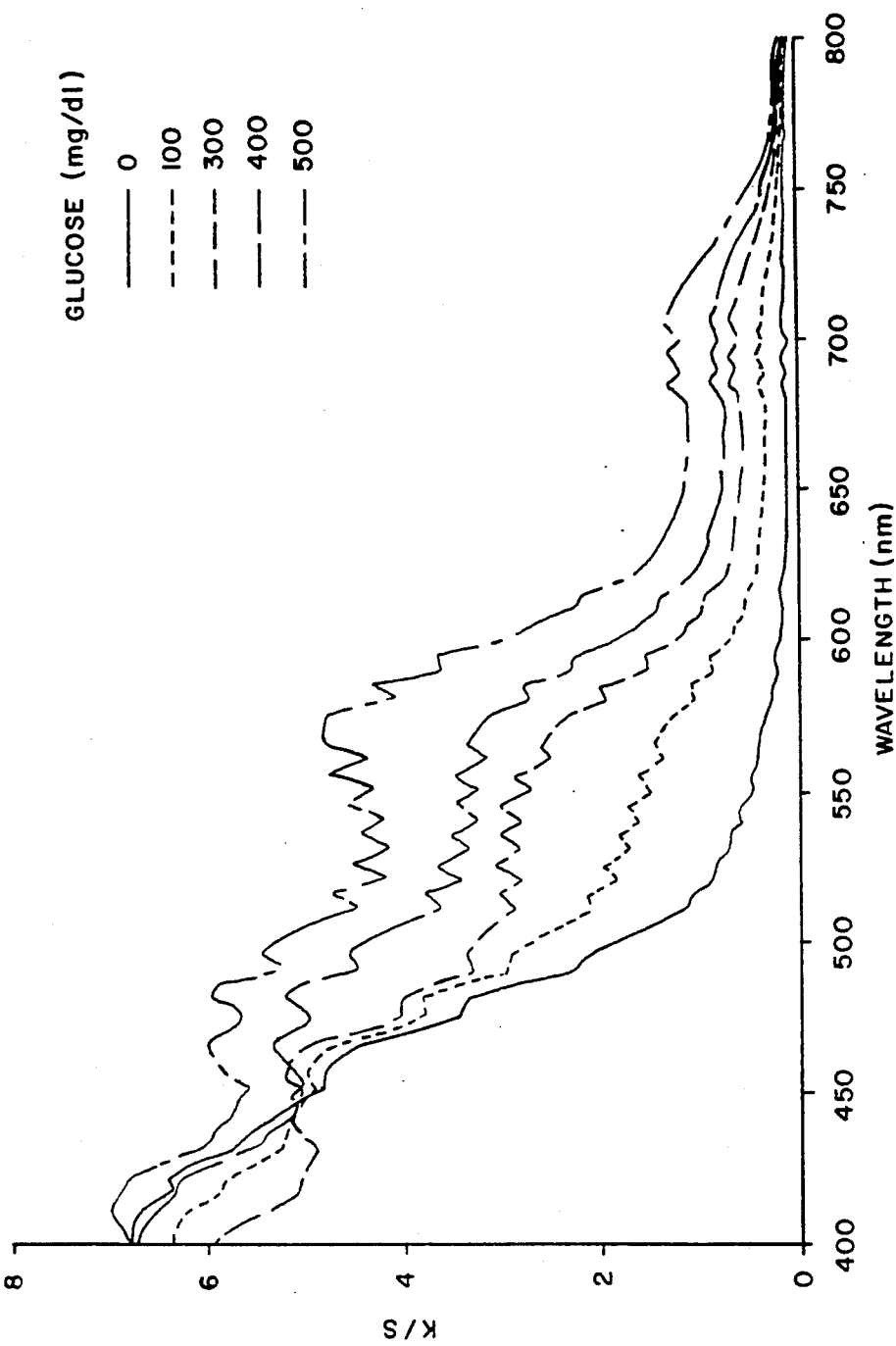
Figure 7:
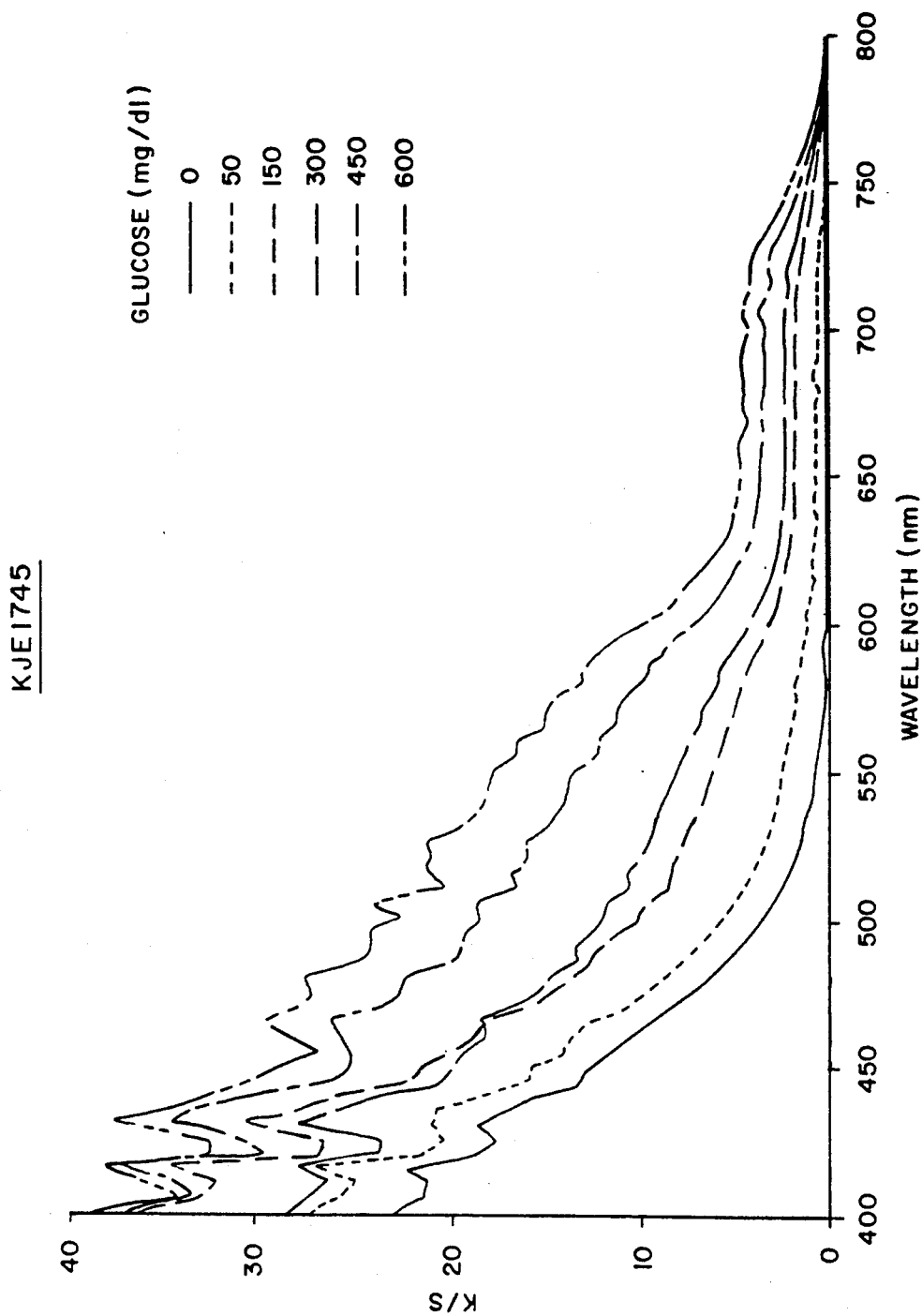
Figure 8:
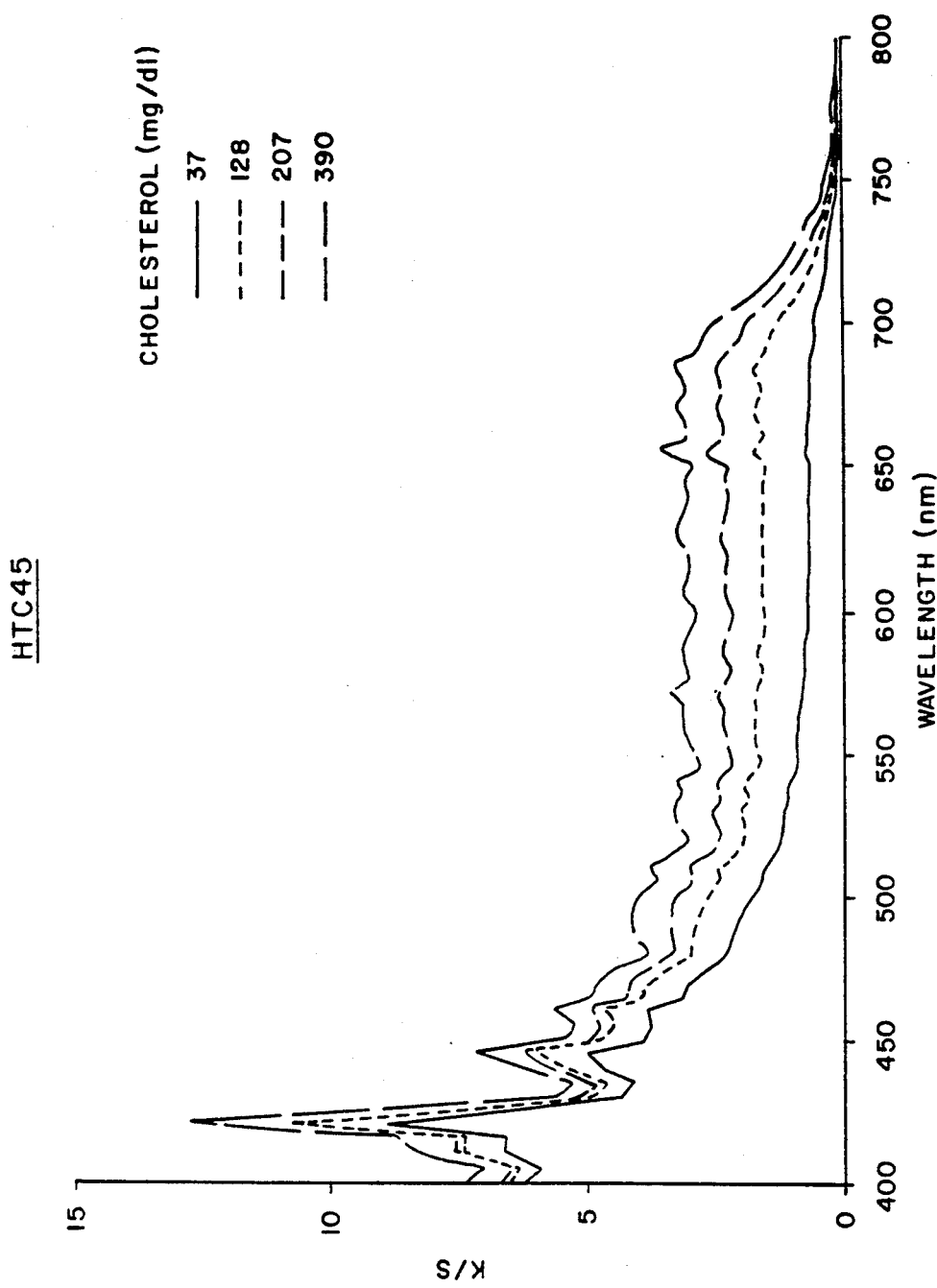
Figure 9:
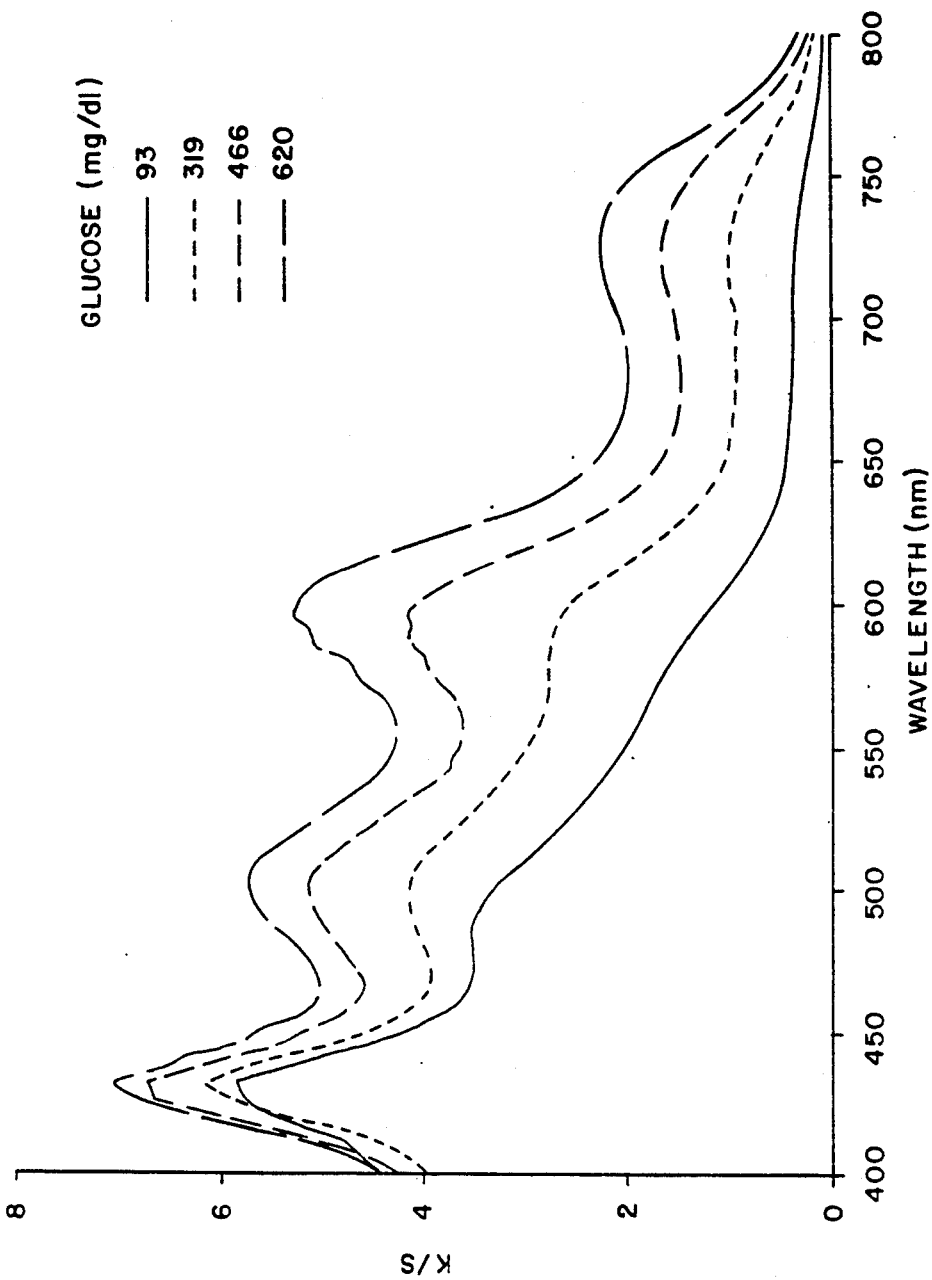

With reference to the drawings, FIGS. 1–4 show the absorption spectra of the formazans produced upon reduction of the prior art tetrazolium salts INT, MTT, and NBT at various concentrations of glucose. For purposes of comparison, FIGS. 5–9 show the corresponding spectra for selected compounds of the present invention. The presence of a plateau in the spectra of the formazans from the present compounds, and its absence from that of the formazans from the prior art compounds is readily apparent.

The four above-mentioned prior art compounds exhibit percent changes in K/S over the wavelength range 650–700 nm as follows:

| | |
| --- | --- |
| INT | 71% |

| | |
|---|---|
| MTT | 178% |
| NBT | 73% |
| USSR | 28% |

The lower the percent K/S value for the formazan, the more tolerant is the tetrazolium salt to variations in the central wavelength of the optical system used to measure reflectance, and hence to measure analyte concentration.

The following non-standard abbreviations are used in the text below:

"UV"—The wavelength in nanometers of maximum reflectance peak in the UV reflectance spectrum of the formazan. The extinction coefficient and solvent used during measurement are given in parentheses.

"nm"—The position of the flatest portion of the reflectance spectrum of the formazan over a 50 nm wavelength span (expressed as the beginning and ending wavelengths in nanometers).

"K/S" The percent change in K/S units over the above mentioned flatest 50 nm portion of the reflectance spectrum. The concentration of analyte used to generate the reflectance spectrum is given in parentheses. Mmol refers to the concentration in mmol/liter.

TABLE

Following is a list of the compounds whose reflectance spectra are shown in FIGS. 5–9 of the drawings. Their shorthand reference number and location in the Table that follows are given in brackets ahead of the compound names.

[LNH50] [A-1-a] 2-(4-Difluoro-5-chlorothiazol-2-yl)-3-(4-methoxyphenyl)-5-[4-(2-(2-(2-ethoxy)-ethoxy)ethoxy)phenyl] tetrazolium salt

[KJE1667] [A-1-d] 2-(4-Difluoro-5-chlorothiazol-2-yl)-3-(4-methoxyphenyl)-5-(3,4-methylenedioxyphenyl) tetrazolium salt

[KJE1745] [A-2-a] 2-(4-Difluoro-5-chlorothiazol-2-yl)-3-(3,4,5-trimethoxyphenyl)-5-(3,4-methylenedioxyphenyl) tetrazolium salt

[HTC45] [A-9-a] 2-(4-difluoro-methyl-5-chlorothiazol-2-yl)-3-(2-methoxyphenyl)-5-(3,4-methylenedioxyphenyl)

[KJE1689] [B-4-a] 2-(4-Trifluoromethyl-5-chlorothiazol-2-yl)-3-(3,4,5-trimethoxyphenyl)-5-(3,4-methylenedioxyphenyl) tetrazolium salt A. 4-difluoromethyl-5-chlorothiazol-2-yl
  1. $R^4$ = 4-methoxyphenyl
    a) $R^3$ = 4-(2-(2-(2-ethoxy)ethoxy)ethoxy)phenyl (LNH50)
      UV: 480 nm (12.8 × 10$^3$, dioxane)
      nm: 645–695 nm; K/S: 6% (17.7 mmol)
      IR(KBr): 2942, 1612, 1504, 1464, 1451, 1261, 1178, 1126, 1061, 837, 658 cm$^{-1}$
      NMR (300 M Hz, DMSO-d$_6$):
      δ 8.24(e, 2H, J=8.8Hz, Ph—OMe), 7.92(d, 2H, J=9.0 Hz, Ph—O—), 7.27–7.33(m, 4H, PhH), 7.26(d, 1H, J=1.04Hz, —CHF$_2$), 4.22–4.32(m, 2H, —CH$_2$O), 3.90(s, 3H, —OMe), 3.20–3.68(m, 10H, —OCH$_2$CH$_2$O—)
      Mass Spectrum (FAB):
      107(100, 135(65.4), 568(4.5, M$^+$—H), 570(1.9, M$^{+1}$)
    b) $R^3$ = 4-(2-(2-(2-methoxy)ethoxy)ethoxy)phenyl
      UV: 468 nm (10.2 × 10$^3$, dioxane)
    c) $R^3$ = 4-(2-(2-(2-hydroxyethoxy)ethoxy)ethoxy)phenyl
      UV: 466 nm (7.6 × 10$^3$, dioxane)
      nm: 645–695 nm; K/S: 5% (11.1 mmol)
    d) $R^3$ = 3,4-methylenedioxyphenyl (KJE1667)
      nm: 650–700 nm; K/S: 7% (11.1 mmol)
  2. $R^4$ = 3,4,5-trimethoxyphenyl
    a) $R^3$ = 3,4-methylenedioxyphenyl (KJE1745)
      UV: 500 (5.66 × 10$^3$, water)
      nm: 665–715 nm; K/S: 5% (17.7 mmol)
      NMR (300 M Hz, DMSO-d$_6$):
      δ 7.91(dd, 1H), 7.82(d, 1H), 7.35(s, 3H), 7.31(t, 1H, CHF$_2$), 7.30(d, 1H), 6.28(s, 2H), 3.79(s, 9H)
      Mass Spectrum (FAB):
      167(71), 330(34), 524(m$^+$, 100)
    b) $R^3$ = 4-(2-(2-(2-hydroxy)ethoxy)ethoxy)phenyl
      UV: 492 nm (3.62 × 10$^3$, dioxane)
      nm: 660–710 nm; K/S: 14% (11.1 mmol)
      IR(KBr): 3436, 1611, 1456, 1384, 1309, 1241, 1180, 1126, 1053, 992 cm$^{-1}$
      NMR (DMSO-d$_6$, 300 M Hz):
      δ 8.26(d, 2H, J=8.89, Ph), 7.40(s, 2H, PhH), 7.33(d, 2H, J=8.90Hz, Ph), 7.30(t, 1H, J=52.3, (HF$_2$), 4.29(dd, 2H, J=5.66, 4.0 Hz, CH$_2$—OH), 3.91 (5.64, —OMe), 3.85(s, 3H, OME), 3.64–3.41(m, 10H, —CH$_2$O)
      Mass Spectrum (FAB) m/e:
      628(13.5), 630(6.0)
  3. $R^4$ = 1-naphthyl
    a) $R^3$ = 4-(2-(2-(2-hydroxyethoxy)-ethoxy)phenyl
      UV: 440 nm (6.32 × 10$^3$, dioxane)
  4. $R^4$ = 1-phenyl
    a) $R^3$ = 4-(2-(2-(2-ethoxy)ethoxy)ethoxy)phenyl
      UV: 474 nm (13.1 × 10$^3$, dioxane)
      nm: 625–675 nm; K/S: 25% (11.1 mmol)
      IR(KBr): 3397, 3004, 2950, 1612, 1452, 1260, 1180, 1127, 1061, 842 cm$^{-1}$
      NMR (300 M Hz, DMSO-d$_6$):
      δ 8.25(d, 2H, J=8.73 Hz, Ph—O—), 8.00(d, 2H, J=7.87 Hz, PhH), 7.88–7.93(m, 1H, PhH), 7.80(d, 2H, J=7.90 Hz, PhH), 7.32(d, 2H, J=8.81 Hz, PhO—), 7.22(d, 1H, J= 104.3Hz, —CHF$_2$), 4.26–4.30 (m, 2H, CHCH$_2$—), 3.79–3,82 (m, 2H, CH$_2$CH$_2$OH), 3.31–3.62 (m, 8H, —OCH$_2$CH$_2$O—)
      Mass Spectrum (FAB):
      301(14.2, 434 (23.9), 538 (35.7 M$^+$ − 1), 539(11.5, M$^+$), 540(15.8, M$^+$ + 1)
  5. $R^4$ = 4-(2-(2-(2-hydroxyethyl)ethoxy)ethoxy)phenyl
    a) $R^3$ = 3,4,5-trimethoxyphenyl
      UV: 516 nm (9 × 10$^3$, H$_2$O)
    b) $R^3$ = 3,4-methylenedioxyphenyl
      UV: 512 nm (13 × 10$^3$, H$_2$O)
  6. $R^4$ = 4-(2-hydroxyethoxy)phenyl
    a) $R^3$ = 3,4-methylenedioxyphenyl
      UV: 492 nm (12 × 10$^3$, H$_2$O)
  7. $R^4$ = 4-(2-(2-hydroxyethyl)ethoxy)phenyl
    a) $R^3$ = 3,4-methylenedioxyphenyl
      UV: 514 nm (11.3 × 10$^3$, H$_2$O)
  8. $R^4$ = 3,4-dimethoxyphenyl
    a) $R^3$ = 3,4-methylenedioxyphenyl
      UV: 410 nm (5.34 × 10$^3$, water)
      nm: 675–725 nm; K/S: 15% (11.1 mmol)

TABLE-continued

Following is a list of the compounds whose reflectance spectra are shown in FIGS. 5-9 of the drawings. Their shorthand reference number and location in the Table that follows are given in brackets ahead of the compound names.

9. $R^4$ = 2-methoxyphenyl
   a) $R^3$ = 3,4-methylenedioxyphenyl (HTC45)
      UV: 610–640 (7.5 × $10^3$)
      nm: 635–685 nm; K/S: 7% (8.2 mmol)
B. 4-trifluoromethyl-5-chlorothiazol-2-yl
   1. $R^4$ = 4-carboxyphenyl
      a) $R^3$ = 4-(2-(2-(ethoxy)ethoxy)ethoxy)phenyl
         UV: 560 nm (5.9 × $10^3$, dioxane)
         nm: 630–680 nm; K/S: 18% (11.1 mmol)
         IR(KBr): 3461, 1612, 1455, 1385, 1263, 1178, 993 $cm^{-1}$
         NMR (300 MHz, DMSO-$d_6$):
         δ 8.20–8.32(m, 5H),
         8.08–8.14(m, 1H, Ph), 7.32
         (3, 1H, J=8.92, —PhH), 7.18
         (d, 1H, J - 8.89, —PhH),
         4.16–4.32(m, 2H, C$\underline{H}$CH$_3$),
         3.39–3.82(m, 8H, ethylene glycol), 1.09(t, 3H, J=6.99, —CH$_3$)
         Mass Spectrum (FAB):
         320(15.6), 436(18.80, 584
         (13.9, $M^+$ — H)
      b) $R^3$ = 4-(2-(2-(2-hydroxyethoxy)ethoxy)ethoxy)phenyl
         UV: 492 nm (5.4 × $10^3$, dioxane)
         nm: 640–690 nm; K/S: 14% (11.1 mmol)
         IR(KBr): 3013, 1610, 1518, 1450, 1203, 1050, 928, 717, 664 $cm^{-1}$
         NMR (300 MHz, DMSO-$d_6$):
         δ 8.24–8.33(m, 4H, PhH),
         8.12(d, 2H, J=8.8 Hz, PhCr2H), 7.32(d, 2H, J=8.9 Hz, PhCO$_2$H), 4.27–4.29(m, 2H, OC$\underline{H}$CH$_2$—), 3.79–3.82(m, 2H, —OC$\underline{H}_2$CH$_2$O), 3.40–3.63 (m, 8H, —O—CH$_2$CH$_2$—O—)
         Mass Spectrum (FAB):
         121(100), 146(29.5), 149
         (26.5), 600(9.6, $M^+$ — H), 602
         (4.2, $M^+$ + 1)
      c) $R^3$ = methoxyphenyl
         nm: 630–680 nm; K/S: 10% (11.1 mmol)
   2. $R^4$ = phenyl
      a) $R^3$ = 3,4-methylenedioxyphenyl
         UV: 520 (water, 4.08 × $10^3$)
         nm: 635–685 nm; K/S: 21% (11.1 mmol)
      b) $R^3$ = 4-(2-2-2-(ethoxy)ethoxy)ethoxy)phenyl
         UV: 580 nm (7.7 × $10^3$, dioxane)
         nm: 625–675 nm; K/S: 0.60 (11.1 mmol)
         IR(KBr): 3582, 3462, 1636, 1614, 1486, 1456, 1384, 1179, 1137, 1051, 993, 986, 848, 765, 745, 691 $cm^{-1}$
         NMR (300 MHz, DMSO-$d_6$):
         δ 8.26(3, 1H, J=8.54Hz, Ph—O—), 8.15(d, 1H, J=8.48, PhO—), 8.00–7.77(m, 5H, —Ph), 7.32(d, 1H, J - 8.73), 7.12(d, 1H, J=8.67, Ph—), 3.34–4.28(m, 10H, ethylene glycol), 1.09(t, 3H, J=6.92, —CH$_3$)
         Mass spectrum (FAB):
         540(M-H)$^+$
      c) $R^3$ = 4-(trimethylammonium)phenyl
         UV: 496 nm (11.4 × $10^3$, dioxane)
   3. 4-nitrophenyl
      a) $R^3$ = 4-(trimethylammonium)phenyl
         UV: 590 nm (4.7 × $10^3$, dioxane)
         nm: 525–575 nm; K/S: 14% (11.1 mmol)
         IR(KBr): 3431, 3065, 1751, 1725, 1486, 1469, 1308, 1209, 1182, 1147, 990 $cm^{-1}$
         NMR (300 MHz, DMSO-$d_6$):
         δ 8.85=8.95 )(m, 1H, Ph—),
         8.59(d, 1H, J = 8.8Hz, PhNO$_2$), 8.47–8.55(m, 1H),
         8.44(d, 1H, J=8.9Hz, PhNO$_2$), 8.22–8.35(m, 2H, PhH), 7.96–8.05(m, 1H, PhH), 7.80–7.87(m, 1H)
         3.75(s, 9H)
         Mass Spectrum (FAB):
         161(100, NCPh$^+$NMR$_3$), 185
         (22.6), 511(12.1, $M^+$)
   4. $R^4$ = 3,4,5-trimethoxyphenyl
      a) $R^3$ = 3,4-methylenedioxyphenyl (KJE1689)
         UV: 500 (water, 6.68 × $10^3$)
         nm: 675–725 nm; K/S: 5% (11.1 mmol)
      b) $R^3$ = 4-acetamidophenyl
         UV: 490 (water, 7.24 × $10^3$)
   5. $R^4$ = 4-(3-dimethylammoniopropylamido-phenyl
      a) $R^3$ = 3,4-methylenedioxyphenyl
         UV: 400 (water)
   6. $R^4$ = 2-methoxy-5-trimethylammoniophenyl
      a) $R^3$ = 3,4-methylenedioxyphenyl
         UV: 540 (water)
   7. $R^4$ = 4-methoxyphenyl
      a) $R^3$ = 3,4-methylenedioxyphenyl
         UV: 500 (water)
   8. $R^4$ = 4-methoxyphenyl
      a) $R^3$ = 3,4-methylenedioxyphenyl
         UV: 500 (water)
   9. $R^4$ = 3,5-dicarboxyphenyl
      a) $R^3$ = 3,4-methylenedioxyphenyl
         nm: 635–685 nm; K/S: 16% (12.2 mmol)
   10. $R^4$ = naphthyl
      a) $R^3$ = 3,4-methylenedioxyphenyl
         nm: 685–735 nm; K/S: 5% (9.4 mmol)
C. 4-carboxyethyl-5-chlorothiazol-2-yl
   1. $R^4$ = 4-methoxyphenyl
      a) $R^3$ = 3,4-methylenedioxyphenyl
         UV: 490 (4.9 × $10^3$, water)
D. 4-carbmethoxy-5-chlorothiazol-2-yl
   1. $R^4$ = phenyl
      a) $R^3$ = 3-thienyl
         UV: 469 (7.66 × $10^3$, water)
      b) $R^3$ = 3,4-methylenedioxyphenyl
         nm: 620–670 nm; K/S: 21% (11.1 mmol)
E. 4-carboxyisopropyl-5-chlorothiazol-2-yl
   1. $R^4$ = phenyl
      a) $R^3$ = 3-thienyl
         UV: 468 (7.8 × $10^3$, water)
   2. $R^4$ = phenyl
      a) $R^3$ = 2-thienyl
         UV: 490 (7.6 × $10^3$, water)
   3. $R^4$ = phenyl
      a) $R^3$ = 3,4-methylenedioxyphenyl
         nm: 625–675 nm; K/S: 6% (9.4 mmol)
F. 4-phenyl-5-carbmethoxythiazol-2-yl
   1. $R^4$ = 4-methoxyphenyl
      a) $R^3$ = 3,4-methylenedioxyphenyl
         UV: 500 (9.82 × $10^3$, water)
   2. $R^4$ = 3,4-dimethoxyphenyl
      a) $R^3$ = 3-thienyl
         UV: 510 (9.76 × $10^3$, water)
   3. $R^4$ = carboxyphenyl
      a) $R^3$ = 3,4-methylenedioxyphenyl
         UV: 500 (5.10 × $10^3$, water)
         nm: 660–710 nm; K/S: 13% (22 mmol)
   4. $R^4$ = 3,4,5-trimethoxyphenyl
      a) $R^3$ = 4-methoxyphenyl
         UV: 500 (9.44 × $10^3$, water)
         nm: 670–720 nm; K/S: 20% (22 mmol)
G. 4-methyl-5-carbmethoxythiazol-2-yl
   1. $R^4$ = 4-carboxyphenyl
      a) $R^3$ = 3,4-methylenedioxyphenyl
         UV: 510 (7.82 × $10^3$, water)

TABLE-continued

Following is a list of the compounds whose reflectance spectra are shown in FIGS. 5-9 of the drawings. Their shorthand reference number and location in the Table that follows are given in brackets ahead of the compound names.

nm: 670-720 nm; K/S: 14% (22 mmol)
  2. $R^4$ = phenyl
  a) $R^3$ = 4-methoxyphenyl
    nm: 650-700 nm; K/S: 14% (9.4 mmol)
  b) $R^3$ = 3-thienyl
    UV: 480 (8.76 × $10^3$, water)
  c) $R^3$ = 3,4-methylenedioxyphenyl
    UV: 500 (6.18 × $10^3$, water)
H. 4-carbmethoxy-5-ethylthiazol-2-yl
  1. $R^4$ = 3,4,5-trimethoxyphenyl
  a) $R^3$ = 3-thienyl
    UV: 500 (7.38 × $10^3$, water)
    nm: 640-690 nm; K/S: 14% (8.3 mmol)
  2. $R^4$ = 3,4,5-trimethoxyphenyl
  a) $R^3$ = 4-methoxyphenyl
    nm: 625-675 nm; K/S: 14% (8.3 mmol)
  b) $R^3$ = 3,4-methylenedioxyphenyl
    UV: 490 (7.96 × $10^3$, water)
    nm: 650-700 nm; K/S: 8% (8.3 mmol)
  3. $R^4$ = 3,4-dimethoxyphenyl
  a) $R^3$ = 3,4-methylenedioxyphenyl
    UV: 490 (5.26 × $10^3$, water)
    nm: 665-715; K/S: 5% (8.3 mmol)
  b) $R^3$ = 3-thienyl
    nm: 635-685 nm; K/S: 11% (8.3 mmol)

The present invention has been particularly described and exemplified above. Clearly, other variations and modifications of the invention can be made without departing from the spirit and scope hereof.

What is claimed is:

1. A compound of the formula:

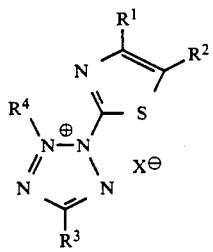

wherein $R^1$ is di- or trifluoroalkyl wherein the fluoro substituents are on the carbon adjacent to the thiazolyl residue in the formula, and $R^2$ is chloro, and wherein $R^3$ is selected from:

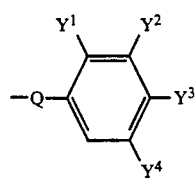

wherein Q is a bond or —CH=CH—, and wherein
(i) $Y^1$ is alkoxy, aryloxy, alkyl, amido, alkylamido, arylamido, alkylthio, arylthio, halo, or hydrogen, $Y^2$ is alkoxy, aryloxy, alkyl, amido, alkylamido, arylamido, alkylthio, arylthio, amino, carbamoyl, carbalkoxy, carboxyl, cyano, halo, hydrogen, nitro, sulfo, sulfonamido, sulfamoyl, trialkylammonio, or ureido, $Y^3$ is alkoxy, aryloxy, alkyl, amido, alkylamido, arylamido, alkylthio, arylthio, amino, carbamoyl, carbalkoxy, carbaryloxy, carboxyl, cyano, halo, hydrogen, hydroxyl, nitro, sulfo, sulfonamido, sulfamoyl, trialkylammonio, or ureido, and $Y^4$ is alkoxy, halo, or hydrogen, or (ii) $Y^2$ and $Y^3$ together form methylenedioxy or imidazo and $Y^1$ and $Y^4$ are hydrogen, (b$_1$) 2, 3, or 4-pyridyl,
(c$_1$) 2, or 3-thienyl, and
(d$_1$) 2 or 3-furanyl;

wherein $R^4$ is selected from:

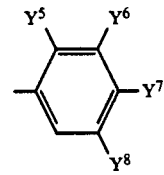

wherein $Y^5$ is alkoxy, aryloxy, alkyl, amido, alkylamido,m arylamido, alkylthio, arylthio, halo, hydrogen, nitro, or ureido, $Y^6$ is alkoxy, aryloxy, alkyl, amido, alkylamido, arylamido, alkylthio, arylthio, carbamoyl, carbalkoxy, carboxyl, cyano, halo, hydrogen, nitro, sulfo, sulfonamido, sulfamoyl, trialkylammonio, or ureido, $Y^7$ is alkoxy, aryloxy, amido, aklylamido, arylamido, alkylthio, arylthio, carbamoyl, carbalkoxy, carbaryloxy, carboxyl, cyano, hydrogen, hydroxyl, nitro, phenylazo, sulfo, sulfonamido, sulfamoyl, or ureido, and $Y^8$ is alkoxy, aryloxy, alkyl, halo, hydrogen or nitro,

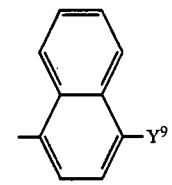

wherein $Y^9$ is alkoxy, aryloxy, alkyl, amido, alkylamido, arylamido, alkylthio, arylthio, carbamoyl, carbalkoxy, carboxyl, cyano, halo, hydrogen, nitro, phenylsulfo, sulfonamido, sulfo, sulfonamido, sulfamoyl, trialkylammonio, or ureido.

(c$_2$) 2, 4, 6, or 8-quinolyl, or 2-methylquinolyl, and
(d$_2$) anthranyl; and wherein X is a counteranion provided that each of the alkyl groups contain from 1 to 6 carbon atoms and that each aryl group is selected from the group consisting of phenyl, naphthyl, pyrydl, oxazolyl, quinolyl, thiazolyl, thienyl and furanyl and further provided that the compounds are characterized in that the reflectance spectra exhibited by each of said compounds when reduced to its colored formazan state varies by less than 17% over a wavelength range of 50 nm at wavelengths of 600 nm or greater.

2. The compound of claim 1 wherein $R^3$ is selected from:

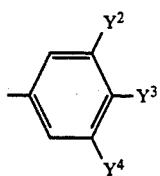

(a₁)

wherein
(i) $Y^2$, $Y^3$, and $Y^4$ are each $C_{1-4}$ alkoxy,
(ii) $Y^4$ is hydrogen and $Y^2$ and $Y^3$ are both $C_{1-4}$ alkoxy or together form methylenedioxy, or
(iii) $Y^2$ and $Y^4$ are both hydrogen and $Y^3$ is $C_{1-4}$ alkoxy, $C_{1-4}$ alkyl, $C_{1-4}$ alkylamido, $C_{1-4}$ alkylthio, carbamoyl, carb($C_{1-4}$)alkoxy, carboxyl, cyano, halo, hydrogen, nitro, tri($C_{1-4}$)alkylammonio, or ureido, and
(b₁) 2 or 3-thienyl;
and wherein $R^4$ is selected from:

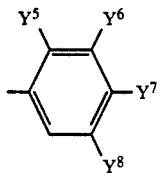

(a₂)

wherein
(i) $Y^5$ is hydrogen and each of $Y^6$, $Y^7$, and $Y^8$ is $C_{1-4}$ alkoxy,
(ii) $Y^5$ and $Y^8$ are both hydrogen and $Y^6$ and $Y^7$ are both $C_{1-4}$ alkoxy or together from methylenedioxy,
(iii) $Y^5$, $Y^6$ and $Y^8$ are each hydrogen and $Y^7$ is $C_{1-4}$ alkoxy, $C_{1-4}$ alkylamido, $C_{1-4}$ alkylthio, benzamido, carbamoyl, carb($C_{1-4}$) alkoxy, carboxyl, cyano, nitro, phenylazo, sulfo, sulfonamido, sulfamoyl, or ureido,
(iv) $Y^5$ is alkoxy or alkyl, $Y^6$ and $Y^8$ are both hydrogen, and $Y^7$ is $C_{1-4}$ alkoxy, $C_{1-4}$ alkylamido, $C_{1-4}$ alkylthio, benzamido, carbamoyl, carb($C_{1-4}$)alkoxy, carboxyl, cyano, hydrogen, nitro, phenylazo, or ureido,
(v) $Y^5$ and $Y^8$ are $C_{1-4}$ alkoxy, or
(vi) $Y^5$ and $Y^8$ are $C_{1-4}$ alkoxy and $Y^7$ is $C_{1-4}$-alkylamido or benzamido;

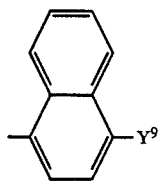

(b₂)

wherein $Y^9$ is $C_{1-4}$ alkoy, $C_{1-4}$ alkyl, $C_{1-4}$ alkylamio, $C_{1-4}$ alkylthio, benzamido, cyano, halo, hydrogen, nitro, sulfo, sulfonamido, or ureido, and (c₂) 8-quinolyl.

3. The compound of claim 2 wherein $R^3$ is selected from:
3,4,5-trimethoxyphenyl,
3,4-dimethoxyphenyl,
3,4-methylenedioxyphenyl,
4-methoxyphenyl,
4-acetamidophenyl,
4-methylthiophenyl,
phenyl,
4-halophenyl,
4-cyanophenyl,
4-nitrophenyl,
2-thienyl, and
3-thienyl,
and wherein
$R^4$ is selected from:
3,4,5-trimethoxyphenyl,
3,4-dimethoxyphenyl,
2,4-dimethoxyphenyl,
3,4-methylenedioxyphenyl,
4-methoxyphenyl,
4-acetamidophenyl,
4-methylthiophenyl,
4-carboxyphenyl,
4-nitrophenyl,
2-methoxyphenyl,
2-methoxy-4-carboxyphenyl,
2,5-dimethoxyphenyl,
2,5-dimethoxy-4-benxamidophenyl,
1-naphthyl,
4-nitro-1-naphthyl,
4-methoxy-1-naphthyl,
8-quinolyl,
2-methyl-4-carboxyphenyl,
4-cyanophenyl, and
4-cyano-1-naphthyl.

4. The compound of claim 1 wherein $R^1$ is di- or trifluoromethyl and $R^2$ is chloro.

5. The compound of claim 4 wherein $R^3$ is selected from:
3,4,5-trimethoxyphenyl,
3,4-dimethoxyphenyl,
3,4-methylenedioxyphenyl,
4-methoxyphenyl,
4-acetamidophenyl,
4-methylthiophenyl,
phenyl,
4-halophenyl,
4-cyanophenyl,
4-nitrophenyl,
3-thienyl,
and wherein
$R^4$ is selected from:
3,4,5-trimethoxyphenyl,
3,4-dimethoxyphenyl,
2,4-dimethoxyphenyl,
3,4-methylenedioxyphenyl,
4-methoxyphenyl,
4-acetamidophenyl,
4-methylthiophenyl,
4-carboxyphenyl,
4-nitrophenyl,
2-methoxyphenyl,
2-methoxy-4-carboxyphenyl,
2,5-dimethoxyphenyl,
2,5-dimethoxy-4-benzamidophenyl,
1-naphthyl,
4-nitro-1-naphthyl,
4-methoxy-1-naphthyl,
8-quinolyl,
2-methyl-4-carboxyphenyl,
4-carbmethoxyphenyl,
4-cyanophenyl, and
4-cyano-1-naphthyl.

6. 2-(4-difluoromethyl-5-chlorothiazol-2-yl)-3-(4-methoxyphenyl)-5-[4-(2-(2-(2-ethoxy)ethoxy)-ethoxy)-phenyl] tetrazolium salt.

7. 2-(4-difluoromethyl-5-chlorothiazol-2-yl)-3-(3,4,5-trimethoxyphenyl) -5-(3,4-methylenedioxyphenyl) tetrazolium salt.

8. 2-(4-difluoromethyl-5-chlorothiazol-2-yl)-3-(4-methoxyphenyl) -5-(3,4-methylenedioxyphenyl) tetrazolium salt 9. 2-(4-difluoromethyl-5-chlorothiazol-2-yl)-3-(2-methoxyphenyl) -5-(3,4-methylenedioxyphenyl) tetrazolium salt.

10. 2-(4-Trifluoromethyl-5-chlorothiazol-2-yl)-3-(3,4,5-trimethoxyphenyl) -5-(3,4-methylenedioxyphenyl) tetrazolium salt.

11. A method for the detection of a reducing substance which comprises contacting one or more of the compounds of claims 1-14 with a fluid suspected of containing a reducing substance and determining whether or not the compound has been reduced to its colored formazan state by observation of a spectral change or lack thereof in the compound.

12. The method of claim 11 wherein the reducing substance is NADH.

13. The method of claim 11 wherein the reducing substance is hydrogen sulfide gas, diborane, arsenic hydride, or phosphorus hydride.

* * * * *